US011478394B2

(12) United States Patent
Tsou et al.

(10) Patent No.: US 11,478,394 B2
(45) Date of Patent: Oct. 25, 2022

(54) EXOSKELETON WEAR MANAGEMENT SYSTEM AND EXOSKELETON WEAR MANAGEMENT METHOD

(71) Applicant: Wistron Corporation, New Taipei (TW)

(72) Inventors: Tsung-Yin Tsou, New Taipei (TW); Min-Yen Li, New Taipei (TW); Tai-Yuan Wang, New Taipei (TW); Hong-Siou Chen, New Taipei (TW)

(73) Assignee: Wistron Corporation, New Taipei (TW)

( * ) Notice: Subject to any disclaimer, the term of this patent is extended or adjusted under 35 U.S.C. 154(b) by 391 days.

(21) Appl. No.: 16/601,549

(22) Filed: Oct. 14, 2019

(65) Prior Publication Data

US 2021/0022943 A1    Jan. 28, 2021

(30) Foreign Application Priority Data

Jul. 22, 2019  (TW) .................................. 108125766

(51) Int. Cl.
 *A61H 3/00*  (2006.01)
 *A61B 5/11*  (2006.01)
 *A61B 5/00*  (2006.01)

(52) U.S. Cl.
 CPC .............. *A61H 3/00* (2013.01); *A61B 5/1116* (2013.01); *A61B 5/486* (2013.01); *A61H 2003/007* (2013.01); *A61H 2201/1207* (2013.01); *A61H 2201/5007* (2013.01); *A61H 2201/5043* (2013.01); *A61H 2201/5069* (2013.01); *A61H 2201/5084* (2013.01)

(58) Field of Classification Search
 CPC .............. A61H 3/00; A61H 2201/5043; A61H 1/0237; A61H 1/0262; A61B 5/1116; B25J 9/0006
 See application file for complete search history.

(56) References Cited

U.S. PATENT DOCUMENTS 9,682,005 B2 *  6/2017  Herr .................... A63B 23/0405
2009/0192414 A1 *  7/2009  Yasuhara ................. A61H 3/00
                                                                600/587

(Continued)

OTHER PUBLICATIONS

Office Action of China Counterpart Application, dated Jul. 22, 2021, pp. 1-11.

*Primary Examiner* — Samchuan C Yao
*Assistant Examiner* — Tyler A Raubenstraw
(74) *Attorney, Agent, or Firm* — JCIPRNET

(57) ABSTRACT

An exoskeleton wear management method is provided. The method includes receiving inertial data from a sensing system; determining whether a left leg component of an exoskeleton device is parallel to a left leg of a user and a right leg component of the exoskeleton device is parallel to a right leg of the user according to the received inertial data; in response to determining that the left leg component/the right leg component is not parallel to the left leg/the right leg of the user, prompting an adjusting left leg component message/an adjusting right leg component message; and in response to determining that the left leg component is parallel to the left leg of the user and the right leg component is parallel to the right leg of the user, prompting a left leg component and right leg component correctly-worn message.

16 Claims, 15 Drawing Sheets

(56) References Cited

U.S. PATENT DOCUMENTS

| | | | | |
|---|---|---|---|---|
| 2013/0237884 | A1* | 9/2013 | Kazerooni | A61H 3/00 601/34 |
| 2014/0221894 | A1* | 8/2014 | Nagasaka | B25J 9/0006 602/23 |
| 2014/0257150 | A1* | 9/2014 | Totman | A61H 31/007 601/41 |
| 2015/0045703 | A1* | 2/2015 | Strausser | A61H 3/00 601/35 |
| 2015/0173929 | A1* | 6/2015 | Kazerooni | A61H 1/0244 602/16 |
| 2016/0229055 | A1* | 8/2016 | Kim | B25J 9/0006 |
| 2016/0253890 | A1* | 9/2016 | Rabinowitz | A61B 5/1112 340/539.13 |
| 2016/0331625 | A1* | 11/2016 | Sankai | A61H 3/00 |
| 2017/0202724 | A1* | 7/2017 | De Rossi | A61H 3/00 |
| 2017/0352240 | A1* | 12/2017 | Carlton-Foss | G08B 21/0446 |
| 2018/0092793 | A1* | 4/2018 | Murakami | A61H 1/0262 |
| 2018/0140842 | A1* | 5/2018 | ÓLaighin | A61N 1/36067 |
| 2018/0272525 | A1* | 9/2018 | Kumeno | B25J 9/1638 |
| 2018/0360347 | A1* | 12/2018 | Lim | A61B 5/112 |
| 2019/0021933 | A1* | 1/2019 | Murakami | A61H 1/00 |
| 2019/0046078 | A1* | 2/2019 | Lim | A61H 1/0237 |
| 2019/0060157 | A1* | 2/2019 | Lamb | B25J 19/0095 |
| 2019/0133866 | A1* | 5/2019 | Tsai | A61H 1/0262 |
| 2019/0262211 | A1* | 8/2019 | Son | A63B 23/0405 |
| 2019/0282429 | A1* | 9/2019 | Son | A61H 1/0237 |
| 2019/0336383 | A1* | 11/2019 | Song | A61H 1/024 |
| 2019/0343707 | A1* | 11/2019 | Riener | A61H 3/00 |
| 2019/0374161 | A1* | 12/2019 | Ly | A61F 2/68 |
| 2019/0380904 | A1* | 12/2019 | Panizzolo | A63B 21/0428 |
| 2020/0060921 | A1* | 2/2020 | Dalley | B25J 13/088 |
| 2020/0179218 | A1* | 6/2020 | Katoh | A61H 3/00 |
| 2020/0281803 | A1* | 9/2020 | Teng | A61H 1/0262 |

\* cited by examiner

EXOSKELETON WEAR MANAGEMENT SYSTEM AND EXOSKELETON WEAR MANAGEMENT METHOD

CROSS-REFERENCE TO RELATED APPLICATION

This application claims the priority benefit of China application serial no. 108125766, filed on Jul. 22, 2019. The entirety of the above-mentioned patent application is hereby incorporated by reference herein and made a part of this specification.

TECHNICAL FIELD

The invention relates to a management system, and more particularly, relates to an exoskeleton wear management system and an exoskeleton wear management method for an exoskeleton device.

BACKGROUND

With the advancement of technology, there are different types of exoskeleton devices (a.k.a. powered exoskeleton devices) on the market. The exoskeleton device can be worn on a user (e.g., installed on upper limbs or/and lower limbs of the user). The limbs of the user on which the exoskeleton device is worn can conduct exercises by an auxiliary force provided by the exoskeleton device to increase exercise capacity for the limbs of the user.

However, because the current process of wearing the exoskeleton device often needs to be performed by a professional, the general public or the user cannot correctly wear the exoskeleton device. As a result, applicability and use efficiency of the exoskeleton device are reduced. In particular, if the exoskeleton device is not correctly worn, the exoskeleton device may perform an incorrect output to decrease work efficiency and increase risk of the user.

Therefore, how to make the exoskeleton device allow the user to correctly wear the exoskeleton device without needing operation and correction of the professional so as to increase applicability and use efficiency of the exoskeleton device, thereby increase work efficiency of the exoskeleton device and reduce risk of using the exoskeleton device is the goal to be achieved by persons skilled in the art.

SUMMARY

The invention provides an exoskeleton wear management system and an exoskeleton wear management method, which can prompt the user of a position of a component among a plurality of components of an exoskeleton device that currently needs to be adjusted so the user can correctly wear the exoskeleton device to thereby improve use efficiency.

An embodiment of the invention provides an exoskeleton wear management system adapted to an exoskeleton device worn on a user. The exoskeleton wear management system includes an exoskeleton wear management device and a sensing system. The exoskeleton wear management device is coupled to the exoskeleton device. The sensing system is installed on the exoskeleton device and coupled to the exoskeleton wear management device, and the sensing system is configured to continuously sense a current posture of the exoskeleton device to output inertial data corresponding to the current posture to the exoskeleton wear management device. The exoskeleton wear management device includes an output device, a storage device and a processor. The storage device stores an exoskeleton wear management code module. The processor is configured to access and execute the exoskeleton wear management code module to realize an exoskeleton wear management method. The processor is configured to receive first inertial data from the sensing system and determine whether the user is in a sitting posture according to the first inertial data, wherein in response to determining that the user is in the sitting posture, the processor is further configured to receive second inertial data, and determine whether a left leg component of the exoskeleton device is parallel to a left leg of the user and a right leg component of the exoskeleton device is parallel to a right leg of the user according to the second inertial data. In response to determining that the left leg component of the exoskeleton device in not parallel to the left leg of the user, the processor is further configured to instruct the output device to prompt an adjusting left leg component message; in response to determining that the right leg component of the exoskeleton device in not parallel to the right leg of the user, the processor is further configured to instruct the output device to prompt an adjusting right leg component message; and in response to determining that the left leg component of the exoskeleton device is parallel to the left leg of the user and the right leg component of the exoskeleton device is parallel to the right leg of the user, the processor is further configured to instruct the output device to prompt a left leg component and right leg component correctly-worn message.

An embodiment of the invention provides an exoskeleton wear management system adapted to an exoskeleton device worn on a user. The exoskeleton wear management system includes an exoskeleton wear management device and a sensing system. The exoskeleton wear management device is coupled to the exoskeleton device. The sensing system includes a plurality of image scanning devices. The plurality of image scanning devices are installed on the exoskeleton device and coupled to the exoskeleton wear management device, wherein each of the plurality of image scanning devices is configured to continuously perform an image scanning operation, and transmit a corresponding message to the exoskeleton wear management device according to a result of the image scanning operation. The exoskeleton wear management device includes an output device, a storage device and a processor. The storage device stores an exoskeleton wear management code module. The processor is configured to access and execute the exoskeleton wear management code module to realize an exoskeleton wear management method. The processor is configured to determine whether the left knee joint component and the right knee joint component of the exoskeleton device are correctly installed on a corresponding left knee joint position and a corresponding right knee joint position according to a plurality of first messages received from the plurality of image scanning devices. In response to not receiving a left knee joint position confirmed message from a left knee joint image scanning device among the plurality of image scanning devices in the plurality of first messages, the processor is further configured to determine that the left knee joint component is not correctly installed on the corresponding left knee joint position, and the processor is further configured to instruct the output device to prompt an adjusting left knee joint component message; in response to not receiving a right knee joint position confirmed message from a right knee joint image scanning device among the plurality of image scanning devices in the plurality of first messages, the processor is further configured to determine that the right knee joint component is not correctly installed on the corresponding right knee joint position, and the processor is further configured to instruct the output device to prompt an adjusting right knee joint component message; in response to receiving the left knee joint position confirmed message and the right knee joint position confirmed message, the processor is further configured to determine that the left knee joint component and the right knee joint component are correctly installed on the corresponding left knee joint position and the corresponding right knee joint position, and determine whether the left hip joint component and the right hip joint component of the exoskeleton device are correctly installed on the corresponding left hip joint position and the corresponding right hip joint position according to a plurality of second messages received from the plurality of image scanning devices. In response to not receiving a left hip joint position confirmed message from a left hip joint image scanning device among the plurality of image scanning devices in the plurality of second messages, the processor is further configured to determine that the left hip joint component is not correctly installed on the corresponding left hip joint position, and the processor is further configured to instruct the output device to prompt an adjusting left hip joint component message; in response to not receiving a right hip joint position confirmed message from a right hip joint image scanning device among the plurality of image scanning devices in the plurality of second messages, the processor is further configured to determine that the right hip joint component is not correctly installed on the corresponding left right joint position, and the processor is further configured to instruct the output device to prompt an adjusting right hip joint component message; in response to receiving the left hip joint position confirmation message and the right hip joint position confirmation message, the processor is further configured to determine that the left hip joint component and the right hip joint component are correctly installed on the corresponding left hip joint position and the corresponding right hip joint position respectively. In addition, in response to determining that the left hip joint component and the right hip joint component are correctly installed on the corresponding left hip joint position and the corresponding right hip joint position respectively, the processor instructs the output device to prompt a wearing-completed message.

An embodiment of the invention provides an exoskeleton wear management method adapted to an exoskeleton wear management system. The exoskeleton wear management system is configured to manage an exoskeleton device worn on a user, wherein the exoskeleton wear management system includes an exoskeleton wear management device and a sensing system. The method includes receiving first inertial data from the sensing system and determining whether the user is in a sitting posture according to the first inertial data; in response to determining that the user is in the sitting posture, receiving second inertial data, and determining whether a left leg component of the exoskeleton device is parallel to a left leg of the user and a right leg component of the exoskeleton device is parallel to a right leg of the user according to the second inertial data; in response to determining that the left leg component of the exoskeleton device in not parallel to the left leg of the user, prompting an adjusting left leg component message; in response to determining that the right leg component of the exoskeleton device in not parallel to the right leg of the user, prompting an adjusting right leg component message; and in response to determining that the left leg component of the exoskeleton device is parallel to the left leg of the user and the right leg component of the exoskeleton device is parallel to the right leg of the user, prompting a left leg component and right leg component correctly-worn message.

An embodiment of the invention provides an exoskeleton wear management method adapted to an exoskeleton wear management system. The exoskeleton wear management system is configured to manage an exoskeleton device worn on a user, wherein the exoskeleton wear management system includes an exoskeleton wear management device and a sensing system, wherein the sensing system includes a plurality of image scanning devices. The method includes determining whether the left knee joint component and the right knee joint component of the exoskeleton device are correctly installed on a corresponding left knee joint position and a corresponding right knee joint position according to a plurality of first messages received from the plurality of image scanning devices; in response to not receiving a left knee joint position confirmed message from a left knee joint image scanning device among the plurality of image scanning devices in the plurality of first messages, determining that the left knee joint component is not correctly installed on the corresponding left knee joint position, and prompting an adjusting left knee joint component message; in response to not receiving a right knee joint position confirmed message from a right knee joint image scanning device among the plurality of image scanning devices in the plurality of first messages, determining that the right knee joint component is not correctly installed on the corresponding right knee joint position, and prompting an adjusting right knee joint component message; in response to receiving the left knee joint position confirmed message and the right knee joint position confirmed message, determining that the left knee joint component and the right knee joint component are correctly installed on the corresponding left knee joint position and the corresponding right knee joint position, and determining whether the left hip joint component and the right hip joint component of the exoskeleton device are correctly installed on the corresponding left hip joint position and the corresponding right hip joint position according to a plurality of second messages received from the plurality of image scanning devices; in response to not receiving a left hip joint position confirmed message from a left hip joint image scanning device among the plurality of image scanning devices in the plurality of second messages, determining that the left hip joint component is not correctly installed on the corresponding left hip joint position, and prompting an adjusting left hip joint component message; in response to not receiving a right hip joint position confirmed message from a right hip joint image scanning device among the plurality of image scanning devices in the plurality of second messages, determining that the right hip joint component is not correctly installed on the corresponding left right joint position, and prompting an adjusting right hip joint component message; in response to receiving the left hip joint position confirmation message and the right hip joint position confirmation message, determining that the left hip joint component and the right hip joint component are correctly installed on the corresponding left hip joint position and the corresponding right hip joint position respectively; and in response to determining that the left hip joint component and the right hip joint component are correctly installed on the corresponding left hip joint position and the corresponding right hip joint position respectively, prompting a wearing-completed message.

In an embodiment of the invention, the sensing system further includes an inertial sensor array and an angle sensor array, wherein in response to determining that the left hip joint component and the right hip joint component are correctly installed on the corresponding left hip joint position and the corresponding right hip joint position respectively, the exoskeleton wear management method further includes performing an exoskeleton output correction operation. The exoskeleton output correction operation includes prompting a stand-up request message; determining whether the user is in a standing posture according to inertial data received from the inertial sensor array; in response to determining that the user is in the standing posture, receiving a plurality of angle data from the angle sensor array, wherein the plurality of angle data include a left hip joint angle value, a right hip joint angle value, a left knee joint angle value and a right knee joint angle value; calculating a plurality of angle difference data according to the plurality of angle data and a plurality of historical angle data in a historical database in the storage device, wherein the plurality of historical angle data include a historical left hip joint angle value, a historical right hip joint angle value, a historical left knee joint angle value and a historical right knee joint angle value, and the plurality of angle difference data include a left hip joint angle difference, a right hip joint angle difference, a left knee joint angle difference and a right knee joint angle difference; in response to one of the plurality of angle difference data greater than a corresponding allowable threshold, prompting a standing posture abnormal message; and in response to all of the plurality of angle difference data not greater than the allowable threshold, adjusting a plurality of output forces of the exoskeleton device corresponding to the plurality of angle difference data according to the plurality of angle difference data, and updating the plurality of historical angle data according to the plurality of angle data.

In an embodiment of the invention, the exoskeleton wear management device further includes an exoskeleton adjusting system. The exoskeleton adjusting system further includes a left stepper motor and a right stepper motor. The exoskeleton wear management method further includes in response to determining that the left hip joint component is not correctly installed on the corresponding left hip joint position, controlling the left stepper motor to change a length of the left leg component; in response to determining that the right hip joint component is not correctly installed on the corresponding right hip joint position, controlling the right stepper motor to change a length of the right leg component; during a period in which the length of the left leg component is changed, in response to receiving the left hip joint position confirmed message, determining that the left hip joint component is correctly installed on the corresponding left hip joint position, and controlling the left stepper motor to stop changing the length of the left leg component; and during a period in which the length of the right leg component is changed, in response to receiving the right hip joint position confirmed message, determining that the right hip joint component is correctly installed on the corresponding right hip joint position, and controlling the right stepper motor to stop changing the length of the right leg component.

Based on the above, according to whether a plurality of components of the exoskeleton device are correctly installed on a plurality of corresponding predetermined positions, the exoskeleton wear management system and the exoskeleton wear management method provided by one embodiment of the invention can prompt the user of one or more components among the plurality of components that need to be adjusted. In addition, the exoskeleton wear management system and the exoskeleton wear management method provided by another embodiment of the invention can directly and automatically adjust the position(s) of the one or more components that need to be adjusted and correct the output of the exoskeleton. As a result, the user can correctly wear the exoskeleton device so that applicability, use efficiency and work efficiency of the exoskeleton device are increased and risk of using the exoskeleton device is reduced.

To make the aforementioned more comprehensible, several embodiments accompanied with drawings are described in detail as follows.

DETAILED DESCRIPTION

First Embodiment

Figure 1A:
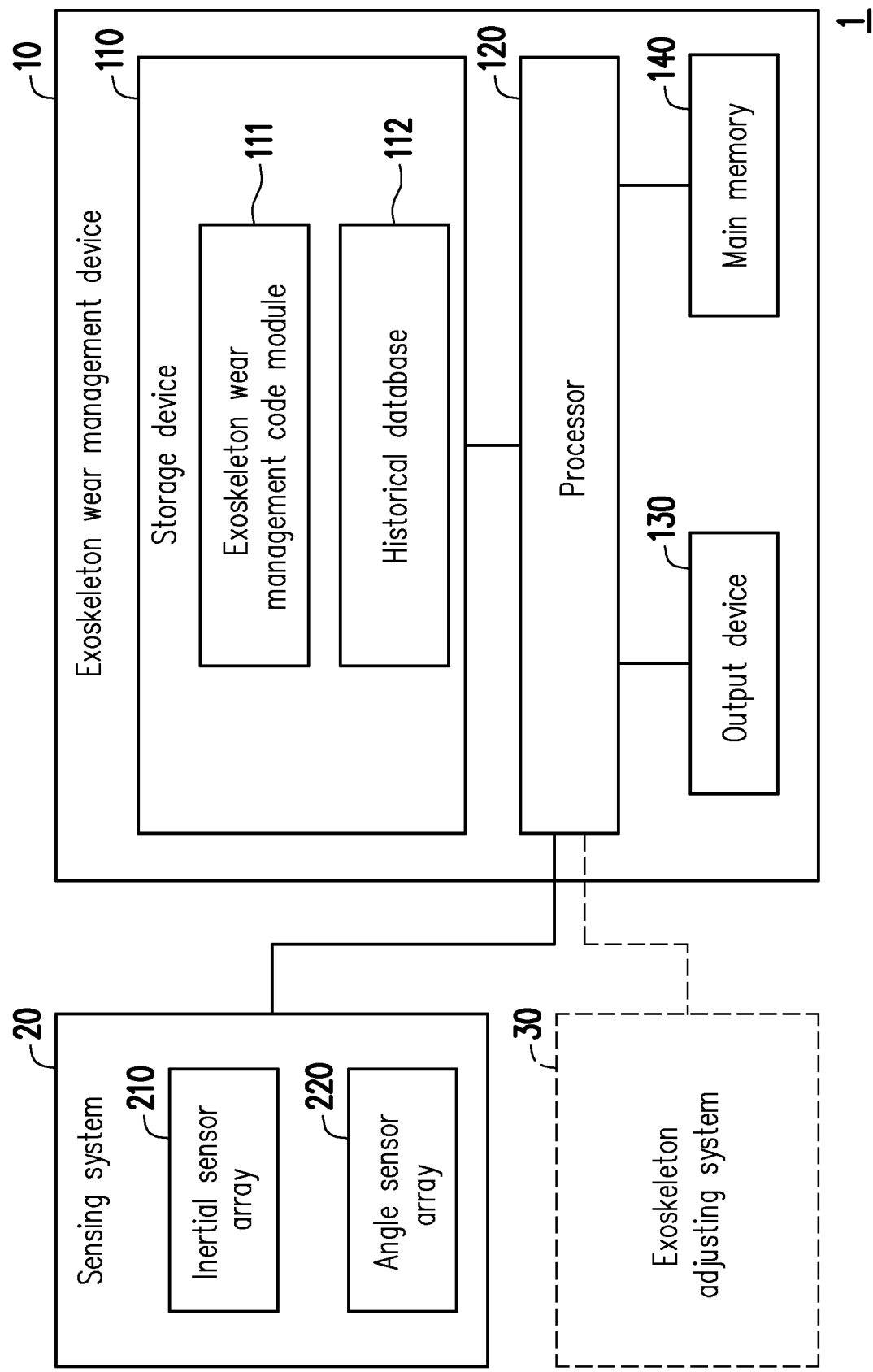
FIG. 1A is a schematic block diagram illustrating an exoskeleton wear management system according to a first embodiment of the invention.

FIG. 1A is a schematic block diagram illustrating an exoskeleton wear management system 1 according to a first embodiment of the invention. With reference to FIG. 1A, in this embodiment, the exoskeleton wear system 1 includes an exoskeleton wear management device 10 and a sensing system 20. In this embodiment, the exoskeleton wear management device includes a storage device 110, a processor 120, an output device 130 and a main memory 140. The sensing system 20 includes an inertial sensor array 210 and an angle sensor array 220. In an embodiment, the exoskeleton adjusting system 30 is coupled (electrically connected) to the processor 120.

The processor 120 is a hardware having a computing capability and configured to manage an overall operation of the exoskeleton wear management device. That is to say, the processor 120 is a main hardware element configured to manage other elements of the exoskeleton wear management device. In this embodiment, the processor 120 is, for example, a central processing unit (CPU) of single-core or multi-core, a micro-processor, other programmable microprocessors, a digital signal processor (DSP), a programmable controller, an application specific integrated circuits (ASIC), a programmable logic device (PLD) or other similar devices.

The storage device 110 can be instructed by the processor 120 to record certain data that need to be stored for a long time, such as firmware or software for controlling the exoskeleton wear management device; one or more code modules; one or more databases. The storage device 110 may be any type of hard disk drive (HDD) or non-volatile memory storage device (e.g., a solid state drive). The one or more code modules include an exoskeleton wear management code module 111. The one or more databases include a historical database 112. The historical database 112 is configured to record a variety of historical data, such as historical angle data. In this embodiment, the historical angle data includes a historical left hip joint angle value, a historical right hip joint angle value, a historical left knee joint angle value and a historical right knee joint angle value.

In this embodiment, the processor 120 can perform an exoskeleton wear management operation by accessing and executing the exoskeleton wear management code module 111 to implement the exoskeleton wear management method provided by the embodiments of the invention.

The output device 130 is configured to output messages. The messages may be a voice message, a text message, an image message or other form of multimedia message. The output device 130 also corresponds to the type of the outputted message. For instance, the output device 130 corresponding to the voice message may be a speaker; the output device 130 corresponding to the text message may be a screen; the output device 130 corresponding to the multimedia message may be a screen with a speaker; the output device 130 corresponding to a light signal message may be an LED light fixture that can display a plurality of LED light signals.

In an embodiment, the exoskeleton wear management device further includes an input device. The input device is, for example, an electronic device for the user 2 to input data by applying an input operation, such as a touch panel. In an embodiment, the output device 130 may also be integrated with the input device. For example, the integrated touch panel can simultaneously provide functions for outputting the messages and receiving touch input operations. In this embodiment, the user 2 can trigger execution of the exoskeleton wear management operation by applying the input operation to the input device.

In this embodiment, the main memory 140 is configured to temporarily store data. The main memory 140 is, for example, a dynamic random access memory. The data includes a firmware for managing the exoskeleton wear management device or a plurality of data obtained by the sensing system 20, but the invention is not limited thereto.

Figure 1B:
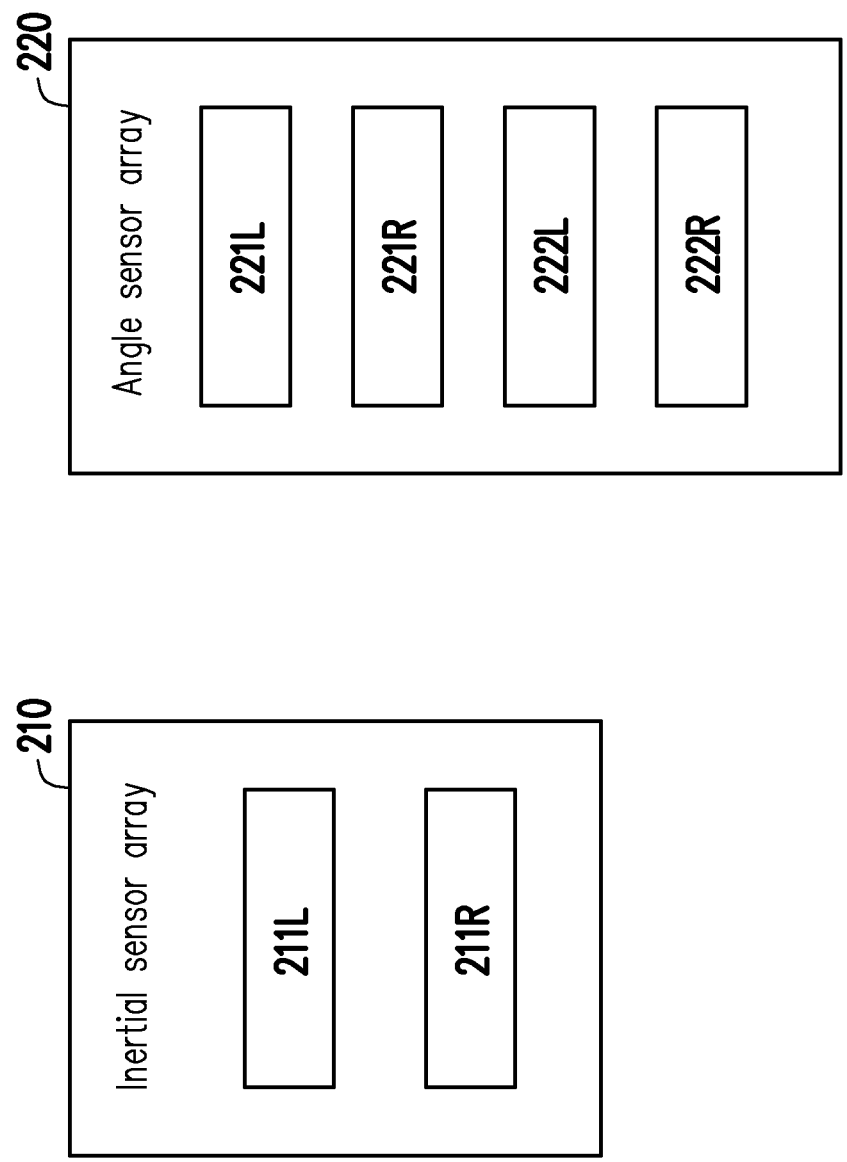
FIG. 1B is a schematic block diagram illustrating an inertial sensor array and an angle sensor array according to the first embodiment of the invention.
Figure 1C:
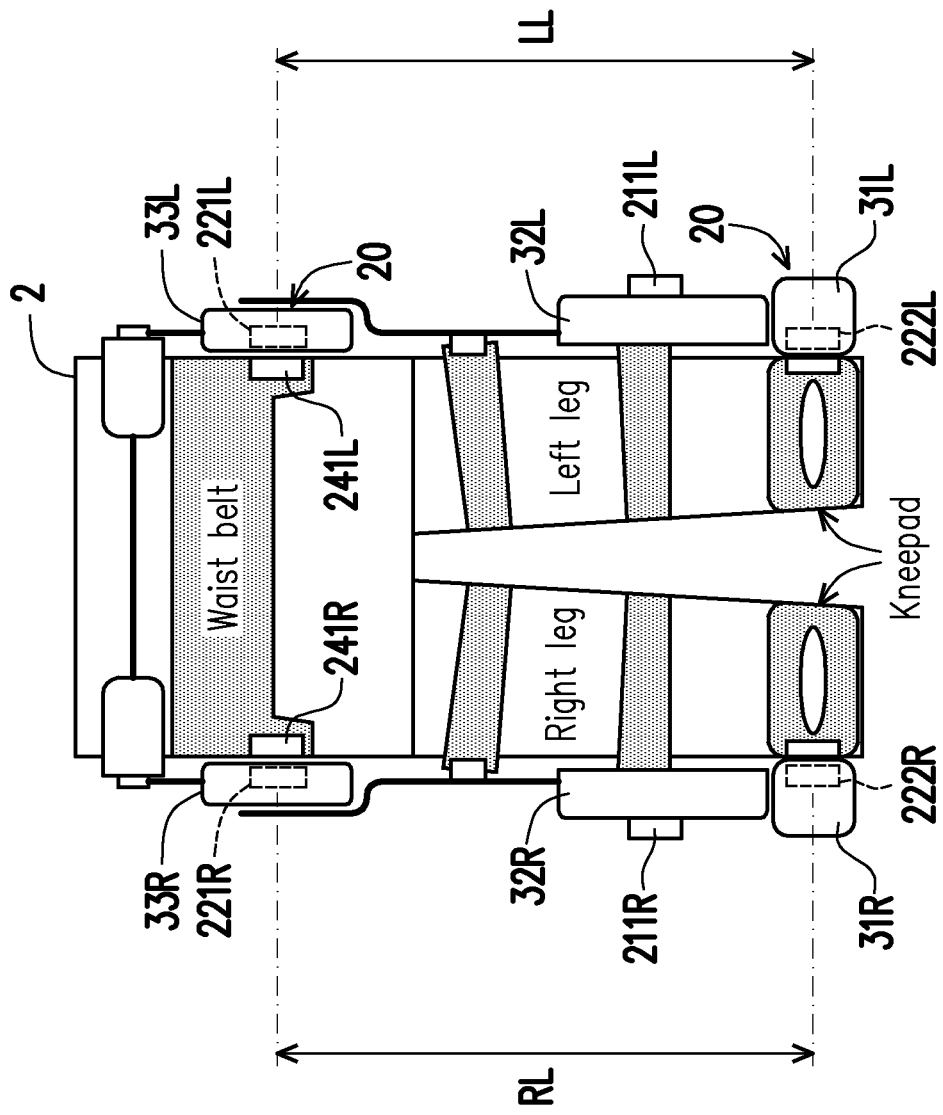
FIG. 1C is a schematic diagram illustrating the exoskeleton wear management system, the exoskeleton device and the user according to the first embodiment of the invention.

FIG. 1B is a schematic block diagram illustrating an inertial sensor array and an angle sensor array according to the first embodiment of the invention. FIG. 1C is a schematic diagram illustrating the exoskeleton wear management system 1, the exoskeleton device and the user 2 according to the first embodiment of the invention. With reference to FIG. 1B and FIG. 1C in this embodiment, the inertial sensor array 210 includes a plurality of inertial sensors 211L and 211R. For example, a left inertial sensor 211L is installed on a leg component 32L of the exoskeleton device and a right inertial sensor 211R is installed on a right leg component 32R of the exoskeleton device. The inertial sensor is configured to detect acceleration vector values of at least three axes (X-axis, Y-axis and Z-axis) of the inertial sensor. The inertial sensor can sense a gravitational acceleration component of each axis read acceleration vector value of the inertial sensor. The inertial sensor is, for example, a 9-axis micro-electromechanical inertial sensor (9-Axis MEMS IMU) or other suitable inertial sensor, but the invention is not limited thereto.

In addition, with reference to FIG. 1B, in the embodiment, the angle sensor array 220 includes a plurality of angle sensors 221L to 222R. For example, the angle sensor 221L is installed on a left hip joint component 33L of the exoskeleton device; the angle sensor 221R is installed on a right hip joint component 33R of the exoskeleton device; the angle sensor 222L is installed on a left knee joint component 31L of the exoskeleton device; the angle sensor 222R is installed on a right knee joint component 31R of the exoskeleton device. In this embodiment, the angle sensor is configured to sense an angle value of the corresponding joint component. That is to say, the angle sensor array 220 of the sensing system 20 is configured to continuously sense a current posture of (a plurality of joint components of) the exoskeleton device and output a plurality of angle data corresponding to the current posture to the exoskeleton wear management device. The angle sensor is, for example, a suitable angle sensor such as a Hall magnetic sensor, but the invention is not limited thereto.

In this embodiment, a distance LL between the left hip joint component 33L and the left knee joint component 31L may also be referred to as a length of a left leg component 32L, and a distance RL between the right hip joint component 33R and the right knee joint component 31R may also be referred to as a length of a right leg component 32R.

Details of the exoskeleton wear management operation performed by the exoskeleton wear management device of the present embodiment and the corresponding implementation of the exoskeleton wear management method will be described below with reference to FIG. 2A.

Figure 2A:
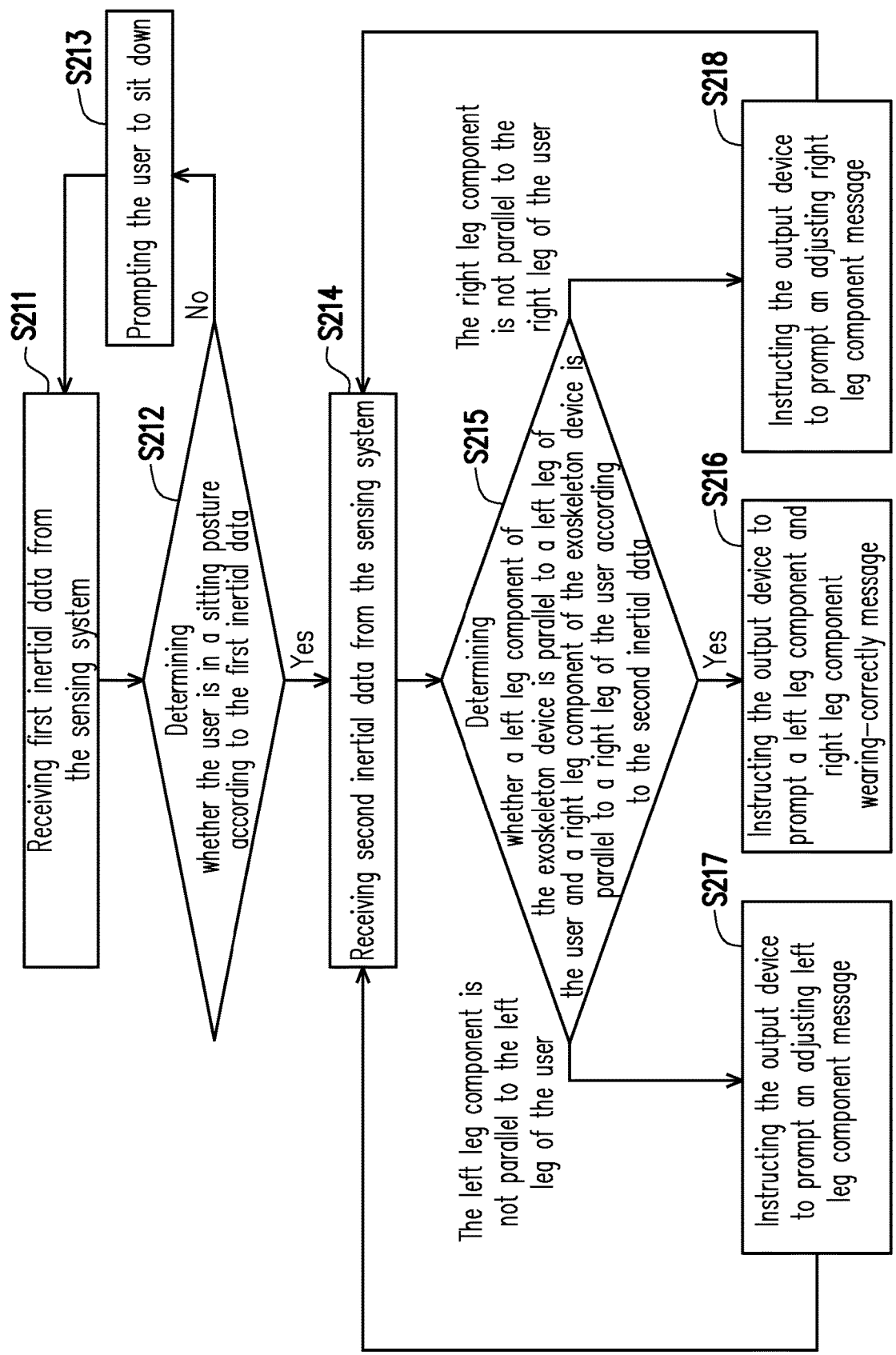
FIG. 2A is a flowchart illustrating an exoskeleton wear management method according to the first embodiment of the invention.

With reference to FIG. 2A, in step S211, the processor 120 receives first inertial data from the sensing system 20. Next, in step S212, the processor 120 determines whether the user 2 is in a sitting posture according to the first inertial data.

Specifically, each of the inertial sensors of the inertial sensor array 210 detects its own posture to output the corresponding inertial data. In this embodiment, the first inertial data includes first left inertial data from the left inertial sensor 211L and first right inertial data from the right inertial sensor 211R. More specifically, the inertial sensor senses components of gravitational accelerations on X-axis, Y-axis and Z-axis of the inertial sensor, and outputs an X-axis component, a Y-axis component and a Z-axis component of the gravitational acceleration on the inertial sensor (a.k.a. an X-axis gravitational acceleration vector, a Y-axis gravitational acceleration vector and a Z-axis gravitational acceleration vector).

Further, in the operation of determining whether the user 2 is in the sitting posture according to the first inertial data, the processor 120 determines whether an X-axis gravitational acceleration absolute value in the first left inertial data is within a predetermined gravitational acceleration range and determines whether an X-axis gravitational acceleration absolute value in the first right inertial data is within the predetermined gravitational acceleration range. In this embodiment, the predetermined gravitational acceleration range is from 0.9 g to 1 g. The X-axis gravitational acceleration absolute value in the first left inertial data is an absolute value of the X-axis gravitational acceleration vector in the first left inertial data; the X-axis gravitational acceleration absolute value in the first right inertial data is an absolute value of the X-axis gravitational acceleration vector in the right left inertial data. It should be noted that the predetermined gravitational acceleration range may also be set to other numerical ranges, but the invention is not limited thereto.

Further, in response to identifying that the X-axis gravitational acceleration absolute value in the first left inertial data is within the predetermined gravitational acceleration range and the X-axis gravitational acceleration absolute value in the first right inertial data is within the predetermined gravitational acceleration range, the processor 120 determines that the user 2 in the sitting posture.

Figure 3A:
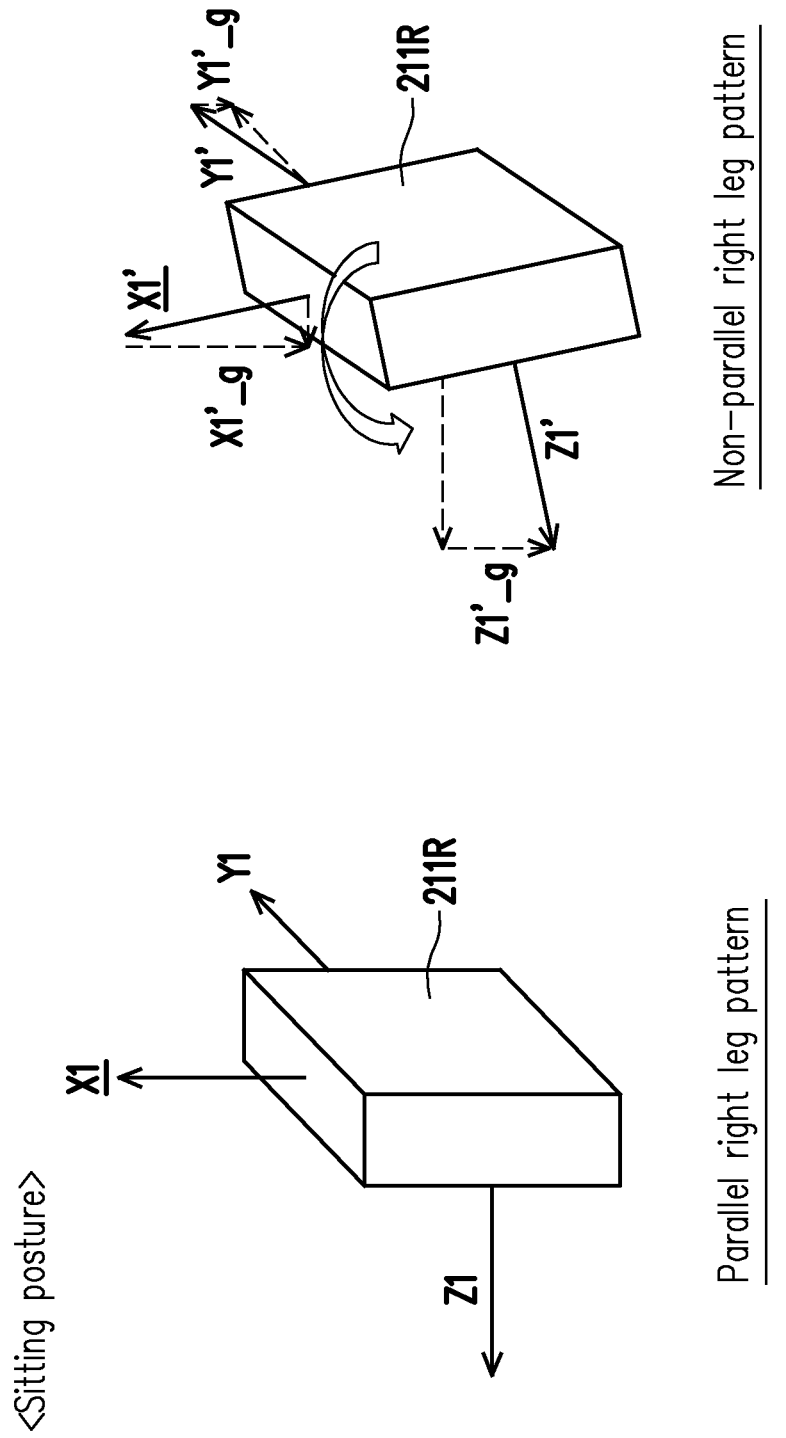
FIG. 3A is a schematic diagram illustrating three-axis acceleration vectors of the inertial sensor when the user is in a sitting posture according to the first embodiment of the invention.
Figure 3B:
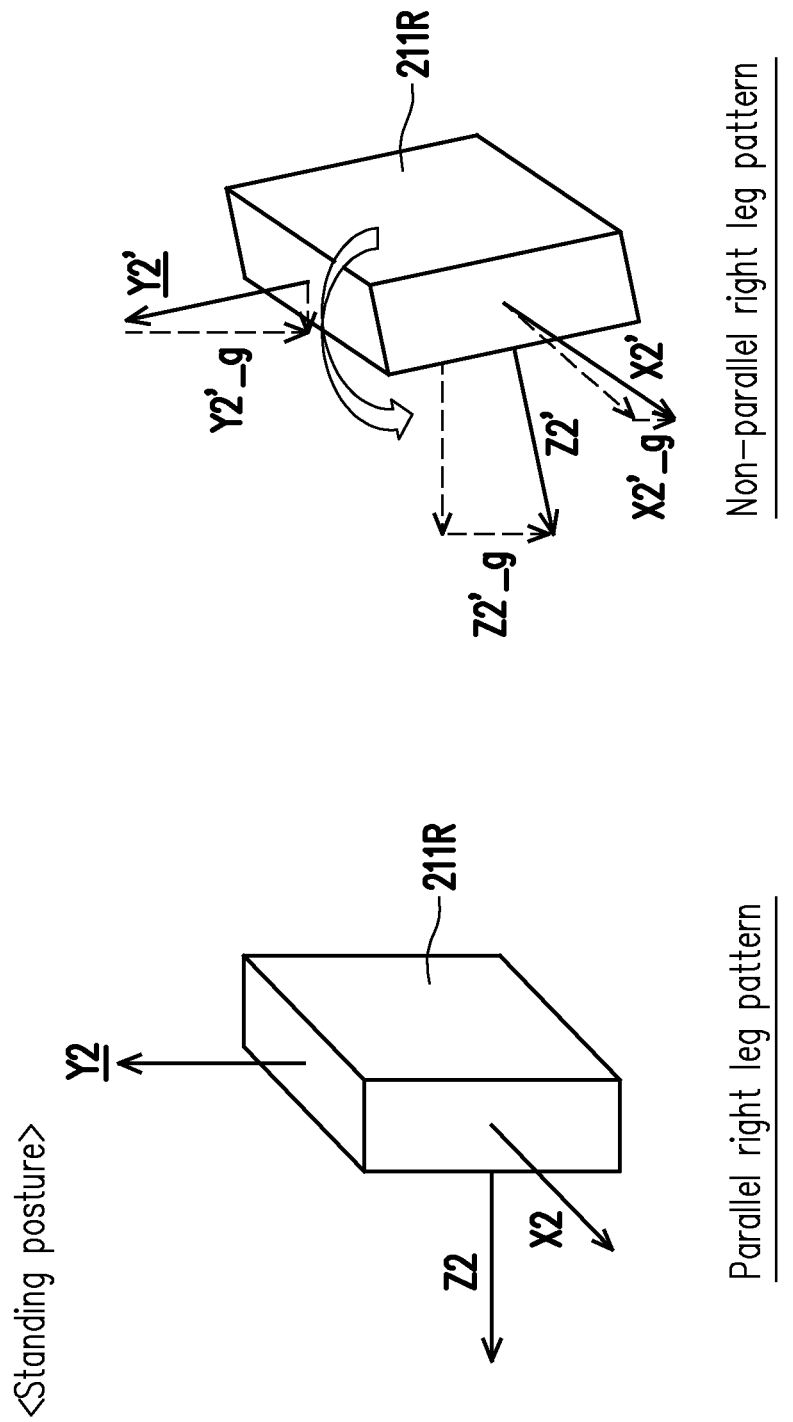
FIG. 3B is a schematic diagram illustrating three-axis acceleration vectors of the inertial sensor when the user is in a standing posture according to the first embodiment of the invention.

FIG. 3A is a schematic diagram illustrating three-axis acceleration vectors of the inertial sensor when the user 2 is in a sitting posture according to the first embodiment of the invention. FIG. 3B is a schematic diagram illustrating three-axis acceleration vectors of the inertial sensor when the user 2 is in a standing posture according to the first embodiment of the invention.

With reference to FIG. 3A, in this embodiment, the right inertial sensor 211R is taken as an example (the right surface of the right inertial sensor 211R in FIG. 3A faces the outer side of the right leg). The right inertial sensor 211R outputs inertial data (a.k.a. right inertial data) having an X-axis gravitational acceleration vector X1, a Y-axis gravitational acceleration vector Y1 and a Z-axis gravitational acceleration vector Z1 (inertial data output by the left inertial sensor 211L may be referred to as left inertial data).

In a parallel right leg pattern on the left in FIG. 3A, because the right inertial sensor 211R and the installed right leg component 32R are parallel to the right leg of the user 2, an absolute value of the X-axis gravitational acceleration vector X1 (a.k.a. the X-axis gravitational acceleration absolute value) of the right inertial sensor 211R is close to 1 g, i.e., falls within the predetermined gravitational acceleration range. It should be noted that in this parallel right leg pattern, an absolute value of the Y-axis gravitational acceleration vector Y1 (a.k.a. a Y-axis gravitational acceleration absolute value) of the right inertial sensor 211R is close to 0 g; an absolute value of the Z-axis gravitational acceleration vector Z1 (a.k.a. a Z-axis gravitational acceleration absolute value) of the right inertial sensor 211R is close to 0 g.

In a non-parallel right leg pattern on the right in FIG. 3A, because the right inertial sensor 211R and the installed right leg component 32R are not parallel to the right leg of the user 2 (e.g., inclined in a direction facing the outer side of the right leg as shown in FIG. 3A), the right inertial sensor 211R outputs right inertial data including an X-axis gravitational acceleration vector X1' (e.g., corresponding to a gravitational acceleration X1'_g), a Y-axis gravitational acceleration vector Y1' (e.g., corresponding to a gravitational acceleration Y1'_g) and a Z-axis gravitational acceleration vector Z1' (e.g., corresponding to a gravitational acceleration Z1'_g). More specifically, the X-axis gravitational acceleration vector X1' is a component of the gravitational acceleration X1'_g; the Y-axis gravitational acceleration vector Y1' is a component of the gravitational acceleration Y1'_g; the Z-axis gravitational acceleration vector Z1' is a component of the gravitational acceleration Z1'_g.

An absolute value of the X-axis gravitational acceleration vector X1' of the right inertial sensor 211R may fall outside of the predetermined gravitational acceleration range (e.g., 0.7 g) or fall within the predetermined gravitational acceleration range. Further, it should be noted that in this example where the user 2 is in the sitting posture and the right inertial sensor 211R is in the non-parallel right pattern, because the right inertial sensor 211R and the installed right leg component 32R are not parallel to the right leg of the user 2, an absolute value of the Y-axis gravitational acceleration vector Y1' (a.k.a. the Y-axis gravitational acceleration absolute value) of the right inertial sensor 211R is greater than 0 g (i.e., the component of the gravitational acceleration is sensed in the Y-axis direction of the right inertial sensor 211R); an absolute value of the Z-axis gravitational acceleration vector Z1' (a.k.a. the Z-axis gravitational acceleration absolute value) of the right inertial sensor 211R is greater than 0 g (i.e., the component of the gravitational acceleration is sensed in the Z-axis direction of the right inertial sensor 211R).

Similarly, with reference to FIG. 3B, in this embodiment, the right inertial sensor 211R is taken as an example (the right surface of the right inertial sensor 211R in FIG. 3B faces the outer side of the right leg). Because the user 2 changes from the sitting posture of FIG. 3A to the standing posture of FIG. 3B (changes from the sitting posture with the X-axis gravitational acceleration vector facing the sky to the standing posture with the Y-axis gravitational acceleration vector facing the sky), the right inertial sensor 211R changes the posture according to a direction from the Y-axis gravitational acceleration vector to the X-axis gravitational acceleration vector. That is to say, the right inertial sensor 211R outputs right inertial data having an X-axis gravitational acceleration vector X2, a Y-axis gravitational acceleration vector Y2, and a Z-axis gravitational acceleration vector Z2.

In a parallel right leg pattern on the left in FIG. 3B, because the right inertial sensor 211R and the installed right leg component 32R are parallel to the right leg of the user 2, an absolute value of the Y-axis gravitational acceleration vector Y2 (a.k.a. the Y-axis gravitational acceleration absolute value) of the right inertial sensor 211R is close to 1 g, i.e., falls within the predetermined gravitational acceleration range. It should be noted that in this parallel right leg pattern, an absolute value of the X-axis gravitational acceleration vector X2 (a.k.a. the X-axis gravitational acceleration absolute value) of the right inertial sensor 211R is close to 0 g; an absolute value of the Z-axis gravitational acceleration vector Z2 (a.k.a. the Z-axis gravitational acceleration absolute value) of the right inertial sensor 211R is close to 0 g.

In a non-parallel right leg pattern on the right in FIG. 3B, because the right inertial sensor 211R and the installed right leg component 32R are not parallel to the right leg of the user 2 (e.g., inclined in a direction facing the outer side of the right leg as shown in FIG. 3B), the right inertial sensor 211R outputs right inertial data including an X-axis gravitational acceleration vector X2' (e.g., corresponding to a gravitational acceleration X2'_g), a Y-axis gravitational acceleration vector Y2' (e.g., corresponding to a gravitational acceleration Y2'_g) and a Z-axis gravitational acceleration vector Z2' (e.g., corresponding to a gravitational acceleration Z2'_g). An absolute value of the Y-axis gravitational acceleration vector Y2' of the right inertial sensor 211R may fall outside of the predetermined gravitational acceleration range (e.g., 0.7 g) or fall within the predetermined gravitational acceleration range. Further, it should be noted that in this example where the user 2 is in the standing posture and the right inertial sensor 211R is in the non-parallel right pattern, an absolute value of the X-axis gravitational acceleration vector X2' (a.k.a. the X-axis gravitational acceleration absolute value) of the right inertial sensor 211R is greater than 0 g (i.e., the component of the gravitational acceleration is sensed in the X-axis direction of the right inertial sensor 211R); an absolute value of the Z-axis gravitational acceleration vector Z2' (a.k.a. the Z-axis gravitational acceleration absolute value) of the right inertial sensor 211R is greater than 0 g (i.e., the component of the gravitational acceleration is sensed in the Z-axis direction of the right inertial sensor 211R).

In other words, the processor 120 can determine that the user 2 is currently in the sitting posture or the standing posture according to the gravitational acceleration absolute values of the left inertial data and the right inertial data within the predetermined gravitational acceleration range determined as the gravitational acceleration absolute value belonging to the X-axis or the Y-axis.

Referring back to FIG. 2A, in response to determining that the user 2 is not in the sitting posture, in step S213, the processor 120 can instruct the output device 130 to prompt the user 2 to sit down. For example, the output device 130 can send the voice message or the text message with the content "Please sit down". Then, the entire process returns to steps S211 and S212 so that whether the user 2 is in the sitting posture is determined again. It should be noted that, in step S213, the processor 120 may wait for a predetermined time (e.g., 10 seconds), and then perform step S211 so the user 2 can change to the sitting posture during the waited predetermined time.

In response to determining that the user 2 is in the sitting posture, in step S214, the processor 120 receives second inertial data from the sensing system 20. Specifically, during a period in which step S214 is performed, inertial data received by the processor 120 from the sensing system 20 may also be referred to as the second inertial data. More specifically, the second inertial data includes N second left inertial data form the left inertial sensor 211L and N second right inertial data from the right inertial sensor 211R, and N is a predetermined positive integer (e.g., 500). For example, in step S214, the processor 120 continuously receives 500 inertial data from the sensing system 20.

Next, in step S215, the processor 120 determines whether the left leg component 32L of the exoskeleton device is parallel to a left leg of the user 2 and the right leg component 32R of the exoskeleton device is parallel to a right leg of the user 2 according to the second inertial data.

Specifically, as described above, when the user 2 is in the sitting posture, if the Y-axis gravitational acceleration absolute value is greater than 0 g or the Z-axis gravitational acceleration absolute value is greater than 0 g, the component where the inertial sensor is installed may be regarded as not being parallel to the leg. Therefore, in step S215, the processor 120 further calculates a Y-axis acceleration absolute average value and a Z-axis acceleration absolute average value corresponding to the N second left inertial data according to the N second left inertial data, and calculates a Y-axis acceleration absolute average value and a Z-axis acceleration absolute average value corresponding to the N second right inertial data according to the N second right inertial data. For example, according to each of Y-axis acceleration absolute values of the 500 second left inertial data, the processor 120 calculates an average value of the 500 Y-axis acceleration absolute values to be the Y-axis acceleration absolute average value corresponding to the 500 second left inertial data; according to each of Z-axis acceleration absolute values of the 500 second left inertial data, the processor 120 calculates an average value of the 500 Z-axis acceleration absolute values to be the Z-axis acceleration absolute average value corresponding to the 500 second left inertial data.

After obtaining the Y-axis acceleration absolute average value and the Z-axis acceleration absolute average value, the processor 120 further determines whether the Y-axis acceleration absolute average value is greater than a Y-axis error threshold, and determines whether the Z-axis acceleration absolute average value is greater than a Z-axis error threshold. The Y-axis error threshold and the Z-axis error threshold may be set to 0.2 g (0.2 times the gravitational acceleration) or other suitable values, but the invention is not limited thereto. Further, in an embodiment, the Y-axis error threshold may be different from the Z-axis error threshold. Also, the smaller the Y-axis acceleration absolute average value and the Z-axis acceleration absolute average value are, the more parallel the components installed with the corresponding inertial sensor are to the corresponding leg.

In response to identifying that the Y-axis acceleration absolute average value corresponding to the second left inertial data is greater than the Y-axis error threshold or the Z-axis acceleration absolute average value corresponding to the second left inertial data is greater than the Z-axis error threshold, the processor 120 determines that the left leg component 32L of the exoskeleton device is not parallel to the left leg of the user 2 (step S215→step S217); in response to identifying that the Y-axis acceleration absolute average value corresponding to the second right inertial data is greater than the Y-axis error threshold or the Z-axis acceleration absolute average value corresponding to the second right inertial data is greater than the Z-axis error threshold, the processor 120 determines that the right leg component 32R of the exoskeleton device is not parallel to the right leg of the user 2 (step S215→step S218).

In step S217, the processor 120 instructs the output device 130 to prompt an adjusting left leg component message. For example, the output device 130 can output the voice message or the text message with the content "The left leg component is not parallel to the left leg, please adjust it".

In step S218, the processor 120 instructs the output device 130 to prompt an adjusting right leg component message. For example, the output device 130 can output the voice message or the text message with the content "The right leg component is not parallel to the right leg, please adjust it".

Further, in response to identifying that the Y-axis acceleration absolute average value corresponding to the second left inertial data is not greater than the Y-axis error threshold and the Z-axis acceleration absolute average value corresponding to the second left inertial data is not greater than the Z-axis error threshold, the processor 120 determines that the left leg component 32L of the exoskeleton device is parallel to the left leg of the user 2; in response to identifying that the Y-axis acceleration absolute average value corresponding to the second right inertial data is not greater than the Y-axis error threshold and the Z-axis acceleration absolute average value corresponding to the second right inertial data is not greater than the Z-axis error threshold, the processor 120 determines that the right leg component 32R of the exoskeleton device is parallel to the right leg of the user 2.

In response to determining that the left leg component 32L of the exoskeleton device is parallel to the left leg of the user 2 and the right leg component 32R of the exoskeleton device is parallel to the right leg of the user 2 (step S215→Yes), in step S216, the processor 120 instructs the output device 130 to prompt a left leg component and right leg component correctly-worn message. For example, the output device 130 can output the voice message or the text message with the content "The left leg component and the right leg component are correctly worn".

In this embodiment, in response to determining that the left leg component 32L of the exoskeleton device is parallel to the left leg of the user 2 and the right leg component 32R of the exoskeleton device is parallel to the right leg of the user 2, the processor 120 further performs a hip joint position management operation.

Figure 2B:
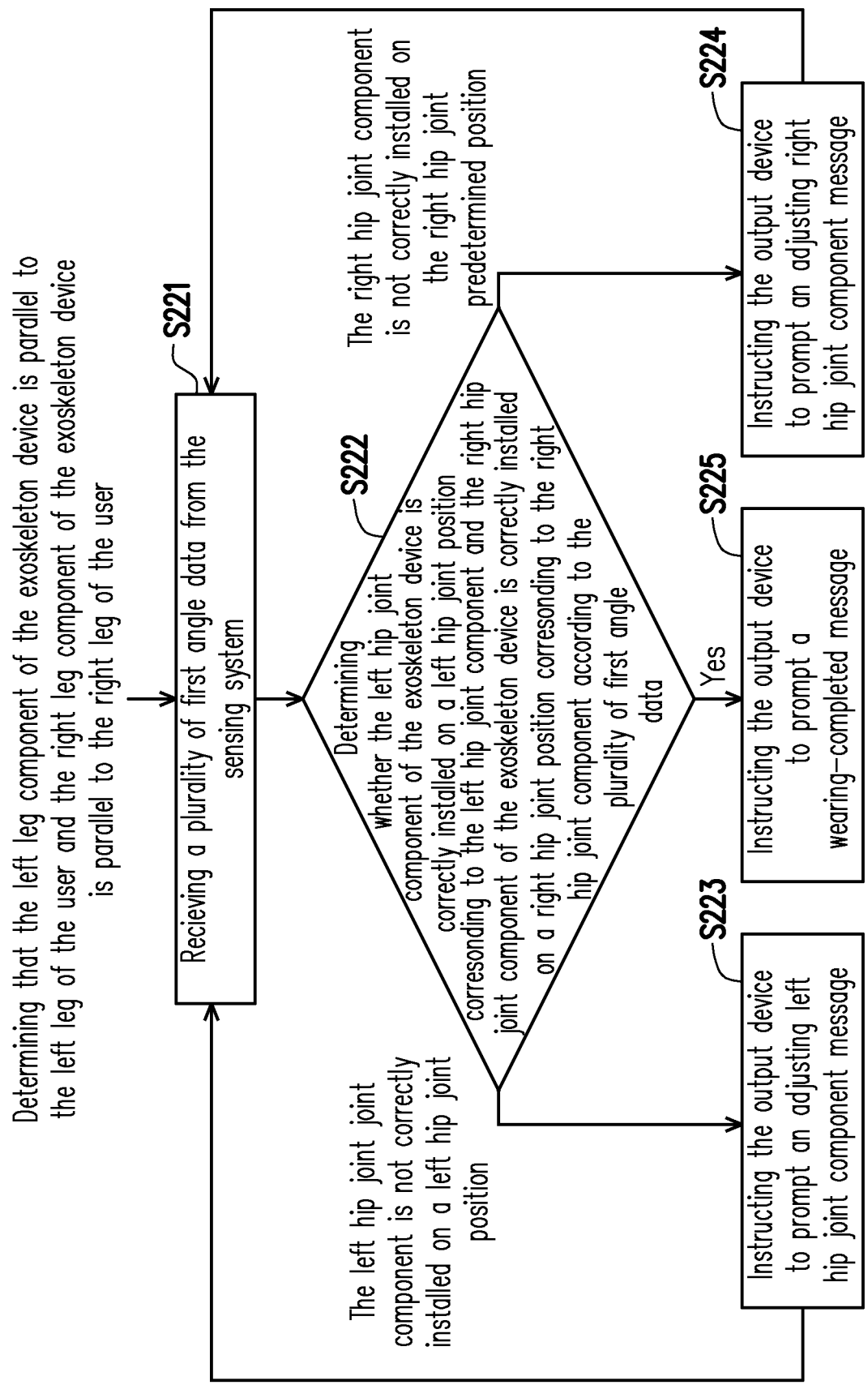
FIG. 2B is a flowchart illustrating a hip joint position management operation according to the first embodiment of the invention.

FIG. 2B is a flowchart illustrating a hip joint position management operation according to the first embodiment of the invention. With reference to FIG. 2B, in step S221, the processor 120 receives a plurality of first angle data from the sensing system 20, wherein the plurality of first angle data include a left hip joint angle value (a.k.a. a first left hip joint angle value) and a right hip joint angle value (a.k.a. a first right hip joint angle value). Next, the processor 120 determines whether the left hip joint component 33L of the exoskeleton device is correctly installed on a left hip joint position corresponding to the left hip joint component 33L and the right hip joint component 33R of the exoskeleton device is correctly installed on a right hip joint position corresponding to the right hip joint component 33R according to the plurality of first angle data. The following embodiment is described with reference to FIG. 3C.

Figure 3C:
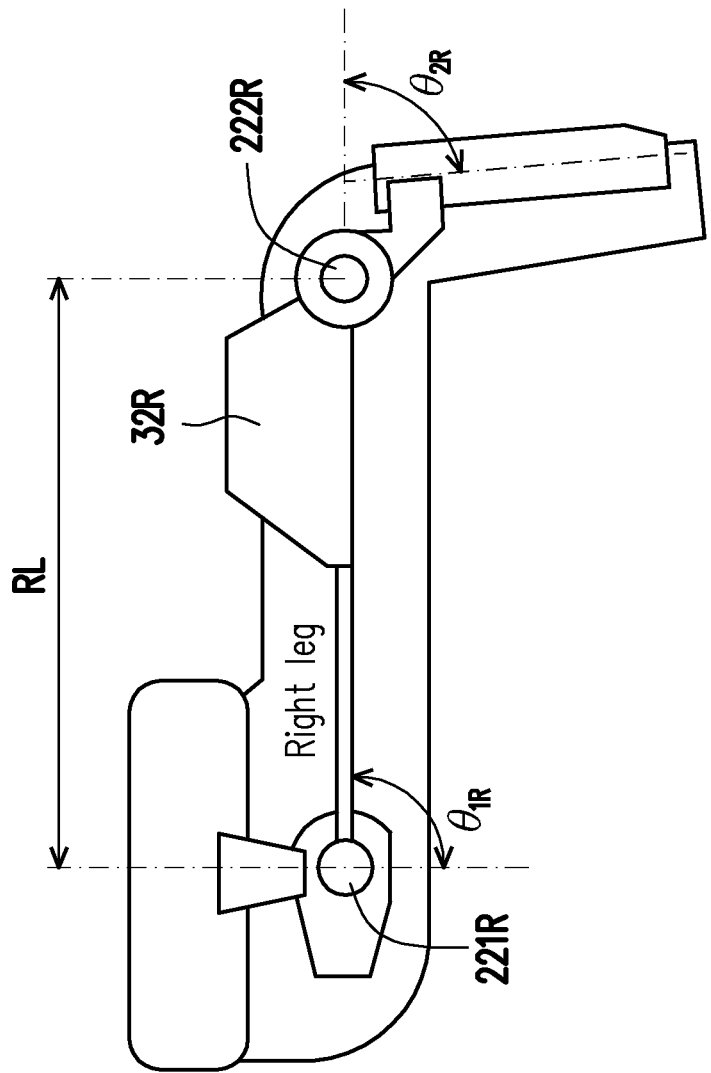
FIG. 3C is a schematic diagram illustrating the angle sensor according to the first embodiment of the invention.

FIG. 3C is a schematic diagram illustrating the angle sensor according to the first embodiment of the invention. With reference to FIG. 3C, the exoskeleton device corresponding to the right leg of the user 2 and the exoskeleton wear management system 1 are taken as an example. The angle sensor 221R installed on the right hip joint component 33R can sense an angle value $\Theta_{1R}$ of the right hip joint component 33R (a.k.a. a right hip joint angle value); the angle sensor 222R installed on the right knee joint component 31R can sense an angle value $\Theta_{2R}$ of the right knee joint component 31R (a.k.a. a right knee joint angle value). On the other hand, the angle sensor 221L installed on the left hip joint component 33L can sense an angle value of the left hip joint component 33L (a.k.a. a left hip joint angle value); the angle sensor 222L installed on the left knee joint component 31L can sense an angle value of the left knee joint component 31L (a.k.a. a left knee hip joint angle value).

In this embodiment, as shown by the example of FIG. 3C, the processor 120 determines whether the right hip joint angle value $\Theta_{1R}$ is within a predetermined angle range, and determines whether the right hip joint angle value $\Theta_{1R}$ is within the predetermined angle range. The predetermined angle range is, for example, 80 degrees to 100 degree (i.e., 90 degree± an error angle value, and the error angle value is, for example, 10 degrees). Further, in response to the right hip joint angle value $\Theta_{1R}$ less than 80 degrees, the processor 120 determines that a length of the right leg component 32R is overly small, and also determines that a position of the right hip joint component 33R should be adjusted by moving in a direction away from the right knee joint component so that the right hip joint component 33R can be installed on a corresponding predetermined position (a.k.a. a right hip joint predetermined position); in response to the right hip joint angle value $\Theta_{1R}$ greater than 100 degrees, the processor 120 determines that the length of the right leg component 32R is overly long, and also determines that the position of the right hip joint component 33R should be adjusted by moving in a direction towards the right knee joint component so that the right hip joint component 33R can be installed on the corresponding predetermined position. It is worth mentioning that in an embodiment, the processor 120 can adjust the positions of the left/right hip joint components by controlling left/right stepper motors 310L/310R in the exoskeleton adjusting system 30. The detailed method will be described in the second embodiment below.

In this embodiment, in response to determining that the left hip joint angle value is within the predetermined angle range, the processor 120 determines that the left hip joint component 33L is correctly installed on a left hip joint predetermined position; in response to determining that the left hip joint angle value is not within the predetermined angle range, the processor 120 determines that the left hip joint component 33L is not correctly installed on the left hip joint predetermined position (step S222→step S223). The left hip joint predetermined position is a predetermined position corresponding to a left hip joint of the user 2 (e.g., the left side of the left hip joint), but the invention is not limited thereto.

Referring back to FIG. 2B, in response to determining that the right hip joint angle value is within the predetermined angle range, the processor 120 determines that the right hip joint component is correctly installed on the right hip joint position; in response to determining that the right hip joint angle value is not within the predetermined angle range, the processor 120 determines that the right hip joint component 33R is not correctly installed on the right hip joint position (step S222→step S224). The right hip joint position is a predetermined position corresponding to a right hip joint of the user 2 (e.g., the right side of the right hip joint), but the invention is not limited thereto.

In this embodiment, in response to determining that the left hip joint component 33L is not correctly installed on the left hip joint position, in step S223, the processor 120 instructs the output device 130 to prompt an adjusting left hip joint component message. The adjusting left hip joint component message is, for example, the voice message or the text message with the content "Installation position of the left hip joint component is incorrect, please adjust it", but the invention is not limited thereto.

In response to determining that the right hip joint component 33R is not correctly installed on the right hip joint position, in step S224, the processor 120 instructs the output device 130 to prompt an adjusting right hip joint component message. The adjusting right hip joint component message is, for example, the voice message or the text message with the content "Installation position of the right hip joint component 33R is incorrect, please adjust it", but the invention is not limited thereto.

It should be noted that, in step S223 and step S224, the processor 120 may wait for another predetermined time, and then perform step S211 so the user 2 can adjust an installation position of the corresponding hip joint component during the waited another predetermined time.

On the other hand, in response to determining that the left hip joint component 33L is correctly installed on the left hip joint position corresponding to the left hip joint component 33L and the right hip joint component 33R is correctly installed on the right hip joint position corresponding to the right hip joint component 33R (step S222→Yes), in step S225, the processor 120 instructs the output device 130 to prompt a wearing-completed message. The wearing-completed message is, for example, the voice message or the text message with the content "The exoskeleton device has been correctly worn", but the invention is not limited thereto.

Further, in this embodiment, in response to determining that the left hip joint component 33L is correctly installed on the left hip joint position corresponding to the left hip joint component 33L and the right hip joint component 33R is correctly installed on the right hip joint position corresponding to the right hip joint component 33R, the processor 120 can further perform an exoskeleton output correction operation to correct an output force of each component of the exoskeleton device according to an angle error value of each joint component of the exoskeleton device by the exoskeleton force correction operation.

Figure 2C:
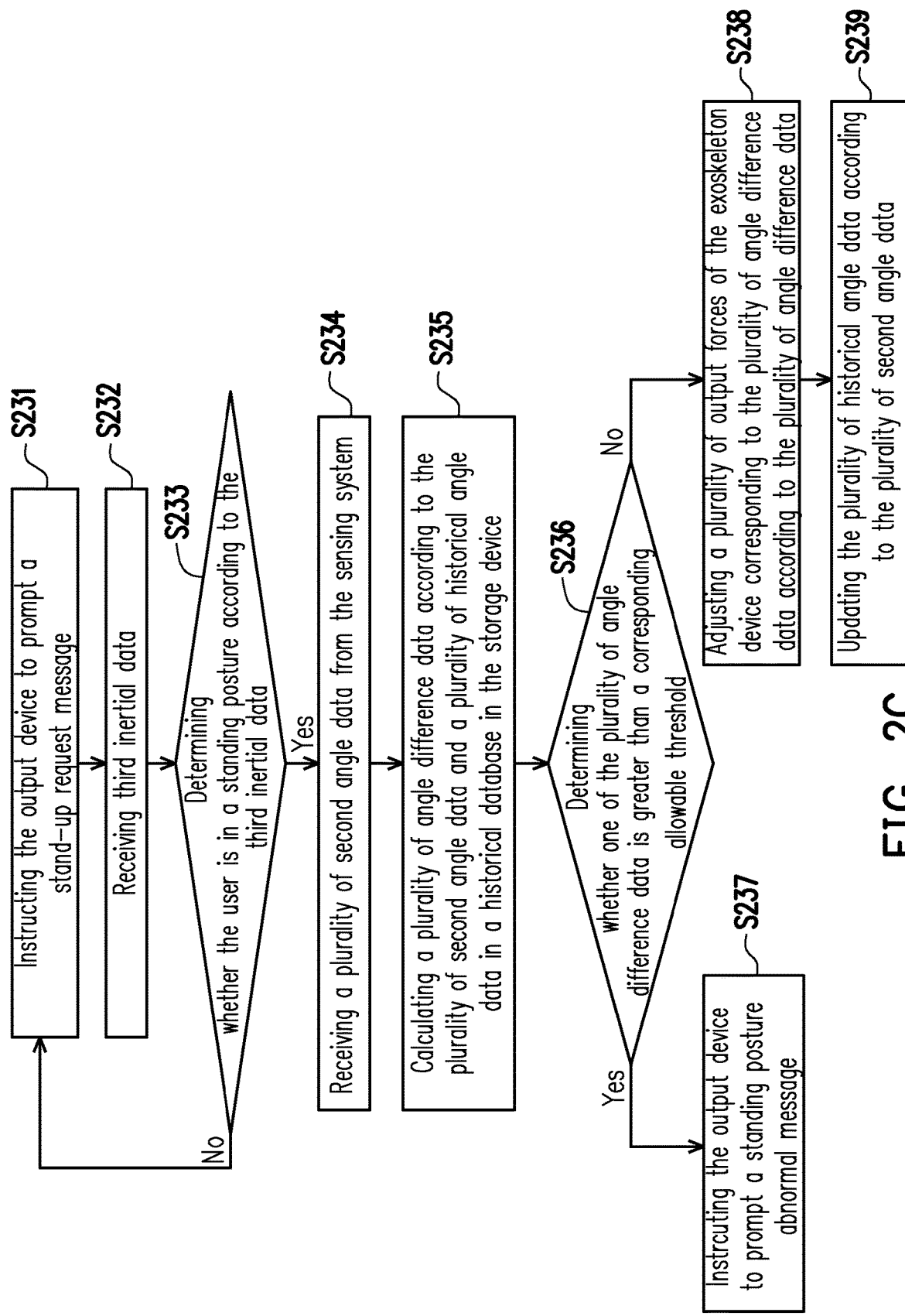
FIG. 2C is a flowchart illustrating an exoskeleton output correction operation according to the first embodiment of the invention.

FIG. 2C is a flowchart illustrating an exoskeleton output correction operation according to the first embodiment of the invention. With reference to FIG. 2C, in step S231, the processor 120 instructs the output device 130 to prompt a stand-up request message. The stand-up request message is, for example, the voice message or the text message with the content "Please stand up", but the invention is not limited thereto.

In step S232, the processor 120 receives third inertial data from the sensing system 20. In other words, after prompting the user to stand up, the processor 120 starts receiving inertial data (a.k.a. the third inertial data) from the inertial sensor array 210 of the sensing system 20.

Next, in step S233, the processor 120 determines whether the user 2 is in the standing posture according to the third inertial data. Specifically, the method of using the inertial data (and the three-axis acceleration vector therein) to determine whether the user us the standing posture has been described above, and will not be repeated hereinafter. In other words, in response to identifying that a Y-axis gravitational acceleration absolute value in third left inertial data is within the predetermined gravitational acceleration range and a Y-axis gravitational acceleration absolute value in third right inertial data is within the predetermined gravitational acceleration range, the processor 120 determines that the user 2 is in the standing posture (step S233→Yes); in response to identifying that the Y-axis gravitational acceleration absolute value in the third left inertial data is not within the predetermined gravitational acceleration range or the Y-axis gravitational acceleration absolute value in the third right inertial data is not within the predetermined gravitational acceleration range, the processor 120 determines that the user 2 is not in the standing posture (step S233→No).

After determining that the user 2 is in the standing posture, in step S234, the processor 120 receives a plurality of second angle data from the sensing system 20. The plurality of second angle data include a left hip joint angle value (a.k.a. a second left hip joint angle value), a left hip joint angle value (a.k.a. a second right hip joint angle value), a left knee joint angle value and a right knee joint angle value.

Next, in step S235, the processor 120 calculates a plurality of angle difference data according to the plurality of second angle data and a plurality of historical angle data in the historical database 112 in the storage device 110. The plurality of angle difference data include a left hip joint angle difference, a right hip joint angle difference, a left knee joint angle difference and a right knee joint angle difference.

For example, the left hip joint angle difference is a difference obtained by calculating the second left hip joint angle value minus the historical left hip joint angle value.

Next, in step S236, the processor 120 determines whether one of the plurality of angle difference data is greater than a corresponding allowable threshold. In this embodiment, the processor 120 sets the corresponding allowable threshold according to different angle differences. If one particular angle difference is greater than the corresponding allowable threshold, the processor 120 then deems that the error is overly great and prompts an abnormal message. For example, in response to one of the plurality of angle difference data greater than the corresponding allowable threshold, (step S236→Yes), in step S237, the processor 120 instructs the output device 130 to prompt a standing posture abnormal message. The standing posture abnormal message is, for example, the voice message or the text message with the content "The user's current standing posture is abnormal, please confirm!", but the invention is not limited thereto.

Further, in response to all of the plurality of angle difference data not greater than the corresponding allowable threshold (step S236→No), in step S238, the processor 120 adjusts a plurality of output forces of the exoskeleton device corresponding to the plurality of angle difference data according to the plurality of angle difference data. Specifically, according to one specific angle difference data among the plurality of angle difference data, the processor 120 can change a previous or preset output force of one or more target components corresponding to the specific angle difference data among the components of the exoskeleton device.

Next, in step S239, the processor 120 updates the plurality of historical angle data according to the plurality of second angle data. Specifically, after adjusting the plurality of output forces corresponding to the plurality of angle difference data, the processor 120 can further record the plurality of adjusted output forces, and update the plurality of historical angle data by using the plurality of second angle data.

Accordingly, by using an exoskeleton output correction operation to correct the output force of each component of the exoskeleton device according to the angle error value of each joint component of the exoskeleton device, the output force of each component of the exoskeleton device can be more adapted to the current posture of the user 2 who wears the exoskeleton device.

Second Embodiment

In the second embodiment, most of the hardware components and corresponding functions and methods have been described in the first embodiment. The following only describes the different parts.

Figure 4A:
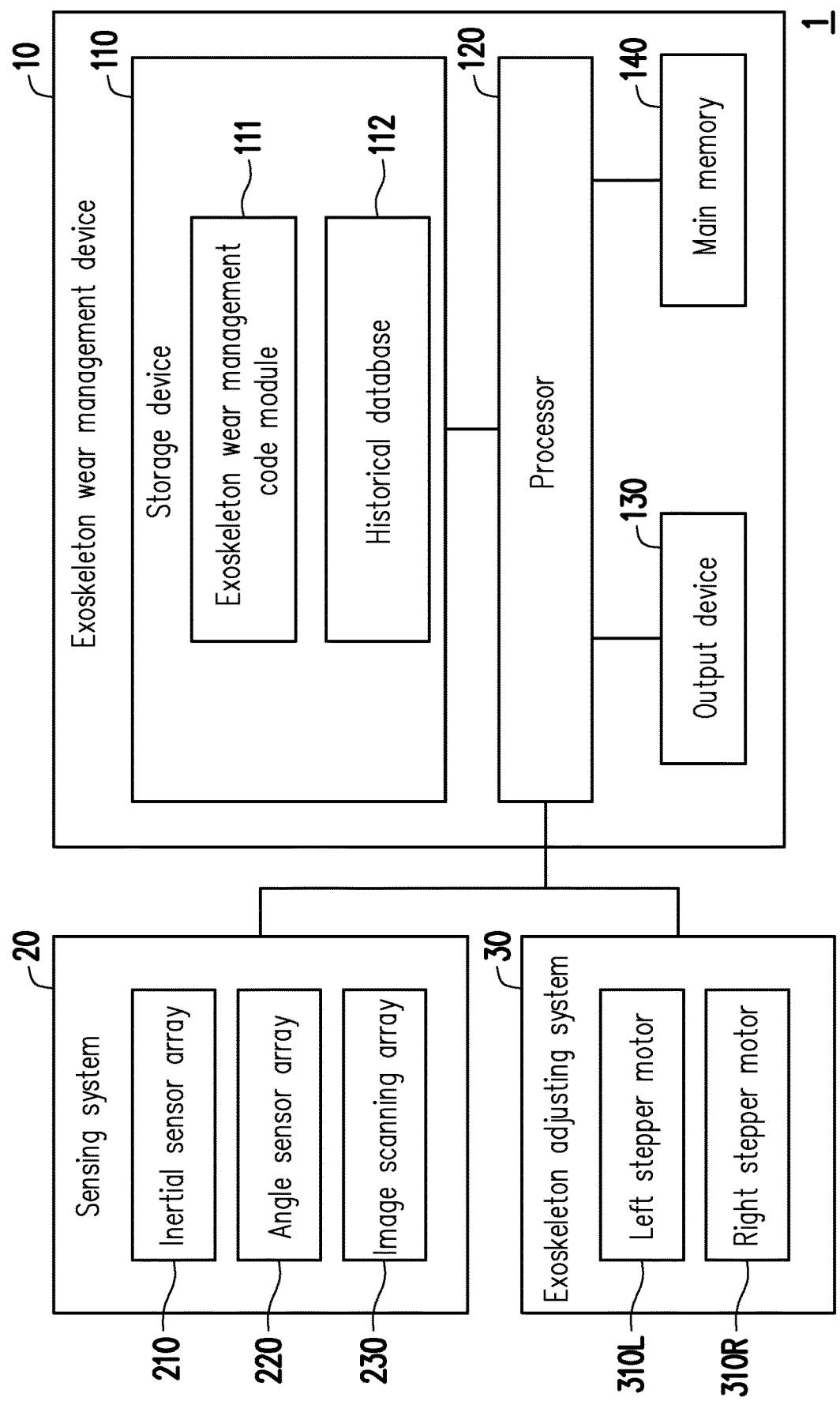
FIG. 4A is a schematic block diagram illustrating an exoskeleton wear management system according to a second embodiment of the invention.

FIG. 4A is a schematic block diagram illustrating an exoskeleton wear management system according to a second embodiment of the invention. With reference to FIG. 4A, the second embodiment is mainly different from the first embodiment in that, the sensing system 20 of an exoskeleton wear management system provided by the second embodiment further includes an image scanning array, and the exoskeleton wear management system 1 further includes the exoskeleton adjusting system 30. The exoskeleton adjusting system 30 further includes a left stepper motor 310L and a right stepper motor 310R. Further, the second embodiment mainly determines whether the exoskeleton device is correctly worn by determining whether a plurality of messages are received from the image scanning array.

Figure 4B:
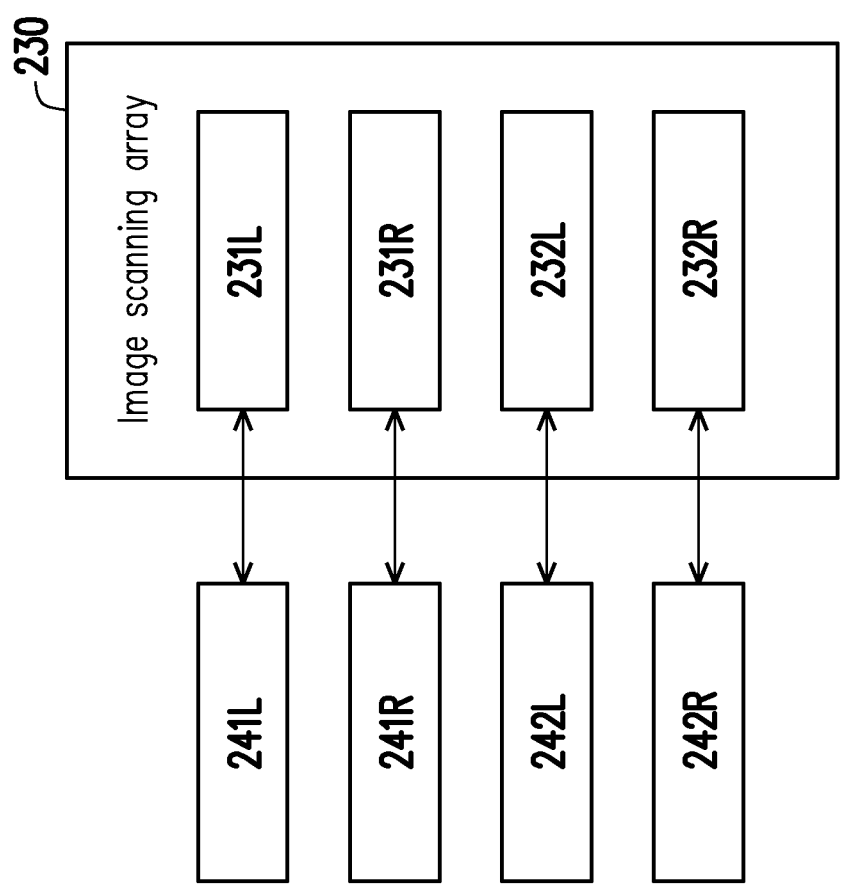
FIG. 4B is a schematic block diagram illustrating an image scanning array and a plurality of corresponding encoded images according to the second embodiment of the invention.

FIG. 4B is a schematic block diagram illustrating an image scanning array and a plurality of corresponding encoded images according to the second embodiment of the invention. With reference to FIG. 4B, the image scanning array includes a plurality of image scanning devices, such as a left hip joint image scanning device 231L, a right hip joint image scanning device 231R, a left knee joint image scanning device 232L and a right knee joint image scanning device 232R. The plurality of image scanning devices 231L, 231R, 232L and 232R are configured to scan corresponding encoded images 241L, 241R, 242L and 242R, respectively, so as to decode the scanned encoded images 241L, 241R, 242L and 242R to thereby obtain corresponding messages, respectively. The following is described with reference to FIGS. 6A and 6B.

Figure 6B:
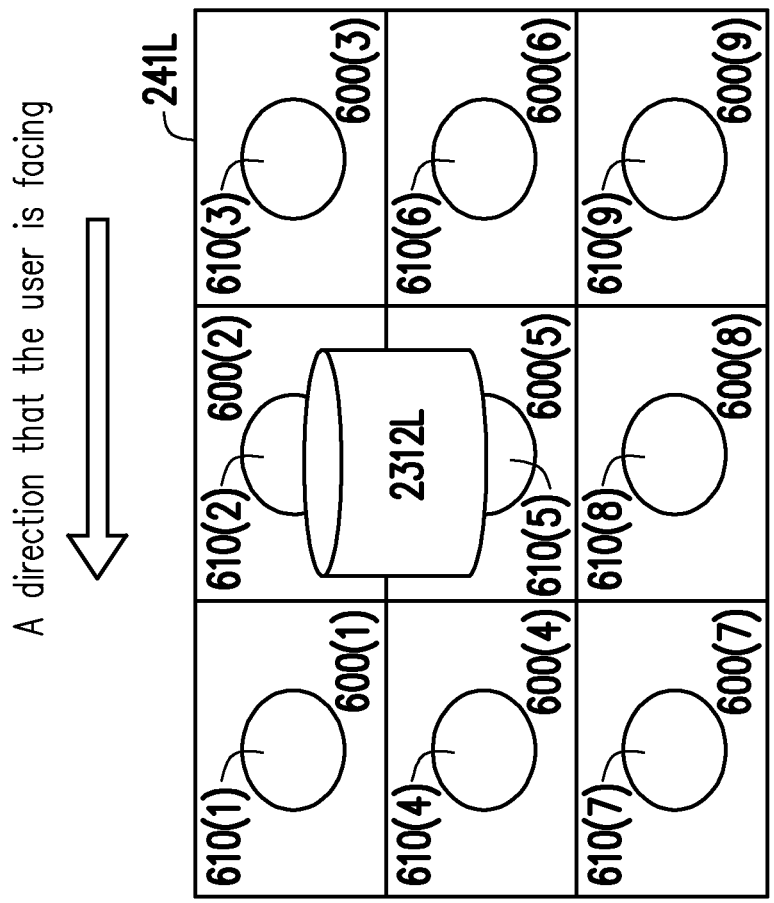
FIG. 6B is a schematic diagram illustrating an image scanning device and the encoded images according to the second embodiment of the invention.
Figure 6A:
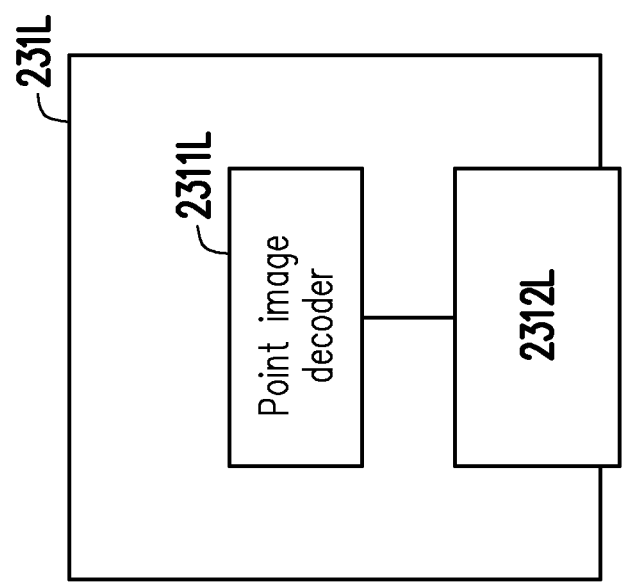
FIG. 6A is a schematic block diagram illustrating image scanning devices according to the second embodiment of the invention.

FIG. 6A is a schematic block diagram illustrating image scanning devices according to the second embodiment of the invention. With reference to FIG. 6A, an image scanning device is used as an example. The image scanning device includes a point image decoder 2311L and an image capturing device 2312L coupled to the point image decoder 2311L.

The image capturing device 2312L is, for example, an electronic device composed of a photosensitive element, a lens and an LED light, which can light up a surface by the LED light to take/capture encoded images printed on the surface.

Each of the encoded images may also be referred to as a point image, which is composed of a plurality of graphical micro-units. The graphical micro-units are so small that can easily be visually ignored or interpreted as a background color by the human eye. The encoded images are drawn on the surface of the corresponding component in the exoskeleton device by ways of printing or the like. The image capturing device 2312L can attempt to capture an image on the surface, and identify a set of the encoded images composed of a plurality of micro image units from the captured image. The point image decoder 2311L can perform a decoding operation on the identified encoded images to identify the messages of the encoded images in the captured image.

FIG. 6B is a schematic diagram illustrating image scanning devices and the encoded images according to the second embodiment of the invention. With reference to FIG. 6B, it is assumed that there are a plurality of sub-regions 600(1) to 600(9) in a set of encoded images 241L corresponding to the image scanning device 231L. According to a direction that user 2 is facing, encoded images 610(1) to 610(9) in the plurality of sub-regions can represent a relative position relation between the left hip joint component 33L corresponding to the image scanning device 231L and a predetermined left hip joint position. For instance, when the encoded image 610(5) is captured by the image capturing device 2312L, the point image decoder 2311L can decode the encoded image 610(5) to obtain a left hip joint position confirmed message. The point image decoder 2311L can transmit the left hip joint position confirmed message to the processor 120.

As another example, when the encoded image 610(2) is captured by the image capturing device 2312L, the point image decoder 2311L can decode the encoded image 610(2) to obtain an overly high left hip joint component position message. The point image decoder 2311L can transmit the overly high left hip joint component position message to the processor 120. After the overly high left hip joint component position message is received by the processor 120, the processor 120 can know that a current installation position of the left hip joint component 33L is overly high and needs to be adjusted to a lower side of the set of encoded images 241L (i.e., needs to adjusted in a direction towards the encoded image 610(5)), i.e., a length of the left leg component 32L needs to be reduced. In other words, when a received message (a.k.a. a joint position confirmed message) is corresponding to the encoded image at the center of the set of encoded images 241L, the processor 120 can determine that the corresponding joint component is correctly installed on a predetermined joint position; When a corresponding joint position confirmed message is not received, the processor 120 can determine that the corresponding joint component is not correctly installed on the predetermined joint position. Also, according to the received message, the processor 120 can further control the exoskeleton adjusting system 30 to move the joint component to the predetermined joint position until the corresponding joint position confirmed message is received.

Figure 7:
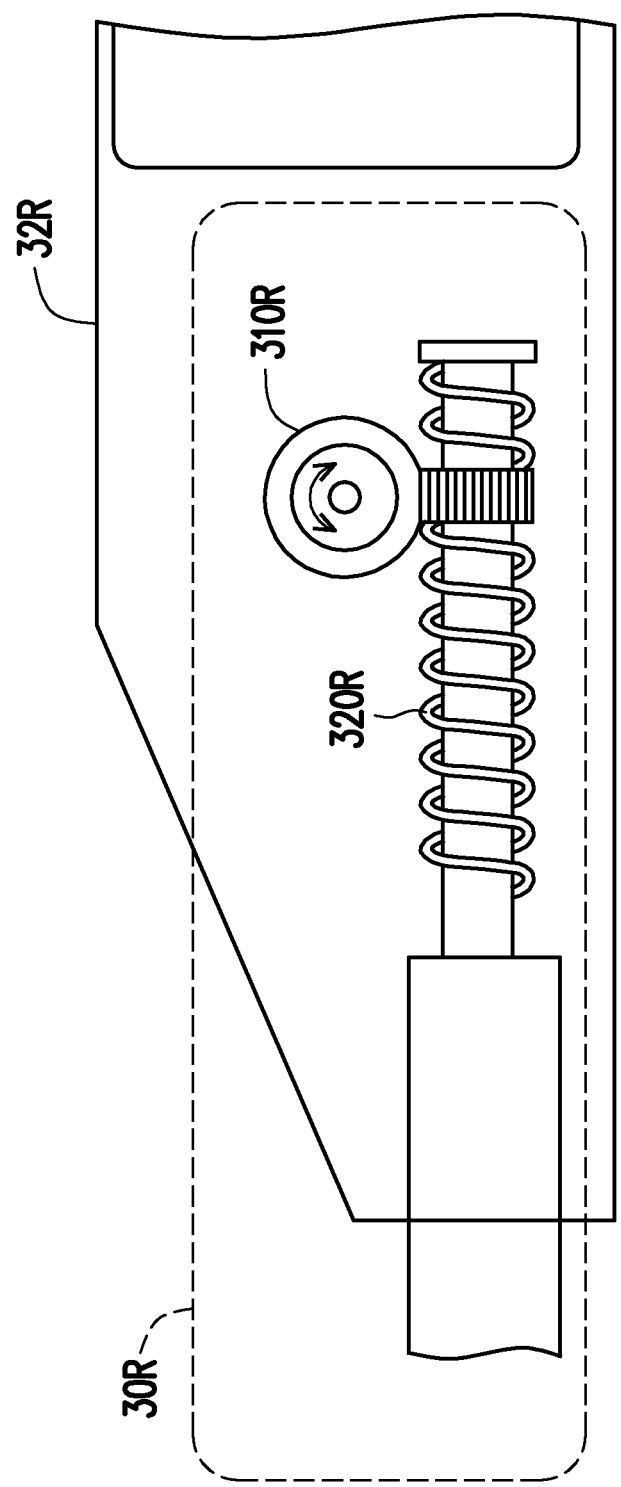
FIG. 7 is a schematic diagram illustrating an exoskeleton adjusting system according to the second embodiment of the invention.

FIG. 7 is a schematic diagram illustrating an exoskeleton adjusting system according to the second embodiment of the invention. With reference to FIG. 7, the right leg component 32R and the exoskeleton adjusting system 30 corresponding to the right leg component 32R are used as an example. The exoskeleton adjusting system 30 corresponding to the right leg component 32R includes the right stepper motor 310R and a right worm gear set 320R. The processor 120 can control a rotation of the stepper motor 310R to change a length of a portion of the right worm gear set 320R exposed outside the right leg component 32R, so as to change the length of the right leg component 32R. Accordingly, an installation position of the right hip joint component 33R may be adjusted.

For example, when the processor 120 determines that the length of the right leg component 32R is overly long, the processor 120 can control the right stepper motor 310R to move the right worm gear set 320R to the right so as to reduce the length of the right leg component 32R.

Figure 8:
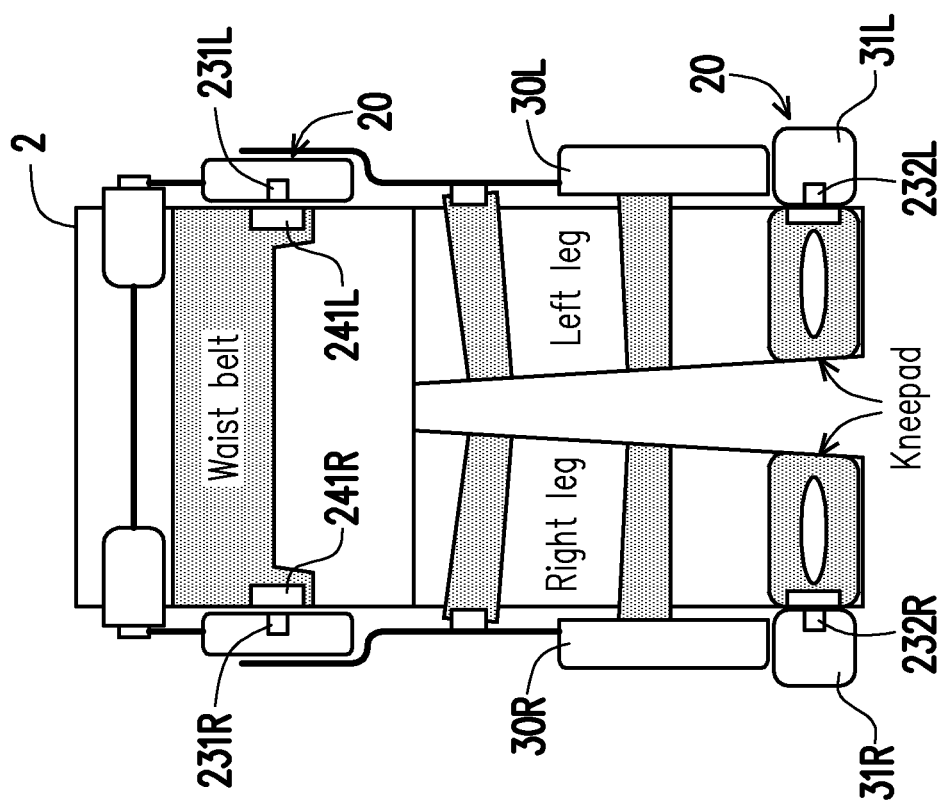
FIG. 8 is a schematic diagram illustrating the exoskeleton wear management system, the exoskeleton device and the user according to the second embodiment of the invention.

The flow of the second embodiment will be described below using FIGS. 5 and 8.

Figure 5:
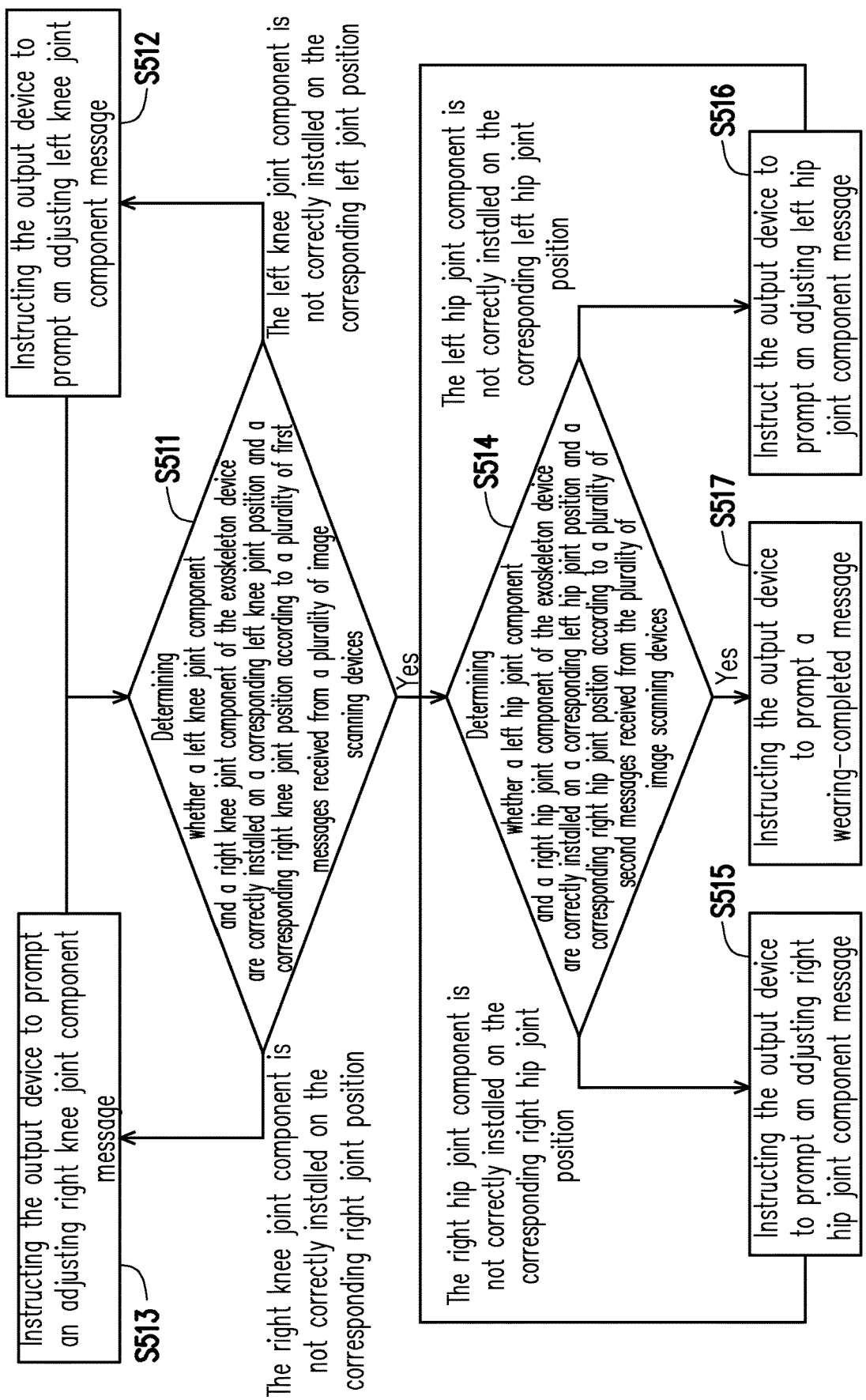
FIG. 5 is a flowchart illustrating an exoskeleton wear management method according to the second embodiment of the invention.

FIG. 5 is a flowchart illustrating an exoskeleton wear management method according to the second embodiment of the invention. FIG. 8 is a schematic diagram illustrating the exoskeleton wear management system, the exoskeleton device and the user according to the second embodiment of the invention. With reference to FIG. 5, in step S511, the processor 120 determines whether the left knee joint component 31L and the right knee joint component 31R of the exoskeleton device are correctly installed on a corresponding left knee joint position and a corresponding right knee joint position according to a plurality of first messages received from a plurality of image scanning devices.

Specifically, in this embodiment, first of all, the processor 120 determines whether the knee joint components are correctly installed (worn) on the corresponding knee joint positions according to whether a left knee joint position confirmed message and a right knee joint position confirmed message are received.

More specifically, when a first encoded image 242L corresponding to the left knee joint image scanning device 232L is scanned by the left knee joint image scanning device 232L, the left knee joint image scanning device 232L decodes the first encoded image 242L to send the left knee joint position confirmed message to the processor 120, wherein the left knee joint position confirmed message is configured to indicate that the left knee joint component 31L is correctly installed on a left knee joint position; when a second encoded image 242R corresponding to the right knee joint image scanning device 232R is scanned by the right knee joint image scanning device 232R, the right knee joint image scanning device 232R decodes the second encoded image 242R to send the right knee joint position confirmed message to the processor 120, wherein the right knee joint position confirmed message is configured to indicate that the right knee joint component 31R is correctly installed on a right knee joint position.

In response to not receiving the left knee joint position confirmed message from the left knee joint image scanning device 232L among the plurality of image scanning devices in the plurality of first messages, the processor 120 is further configured to determine that the left knee joint component is not correctly installed on the corresponding left knee joint position (step S511→step S512). In step S512, the processor 120 is further configured to instruct the output device 130 to prompt an adjusting left knee joint component message.

In response to not receiving the right knee joint position confirmed message from the right knee joint image scanning device 232R among the plurality of image scanning devices in the plurality of first messages, the processor 120 is further configured to determine that the right knee joint component 31R is not correctly installed on the corresponding left knee joint position (step S511→step S513). In step S513, the processor 120 is further configured to instruct the output device 130 to prompt an adjusting right knee joint component message.

In response to receiving the left knee joint position confirmed message and the right knee joint position confirmed message, the processor 120 is further configured to determine that the left knee joint component and the right knee joint component 31R are correctly installed on the corresponding left knee joint position and the corresponding right knee joint position (step S511→Yes). In step S514, the processor 120 determines whether the left hip joint component 33L and the right hip joint component 33R of the exoskeleton device are correctly installed on the corresponding left hip joint position and the corresponding right hip joint position according to a plurality of second messages received from the plurality of image scanning devices.

More specifically, when a third encoded image 241L corresponding to the left hip joint image scanning device 231L is scanned by the left hip joint image scanning device 231L, the left hip joint image scanning device 231L decodes the third encoded image 241L to send the left hip joint position confirmed message to the processor 120, wherein the left hip joint position confirmed message is configured to indicate that the left hip joint component 33L is correctly installed on the left hip joint position; When a fourth encoded image 241R corresponding to the right hip joint image scanning device 231R is scanned by the right hip joint image scanning device 231R, the right hip joint image scanning device 231R decodes the fourth encoded image 241R to send a right hip joint position confirmed message to the processor 120, wherein the right hip joint position confirmed message is configured to indicate that the right hip joint component 33R is correctly installed on the right hip joint position.

In response to not receiving the left hip joint position confirmed message from the left hip joint image scanning device 231L among the plurality of image scanning devices in the plurality of second messages, the processor 120 is further configured to determine that the left hip joint component 33L is not correctly installed on the corresponding left hip joint position (step S514→step S516). In step S516, the processor 120 is further configured to instruct the output device 130 to prompt the adjusting left hip joint component message. Further, in an embodiment, the processor 120 can also control the left stepper motor 310L to change the length of the left leg component 32L. During a period in which the length of the left leg component 32L is changed, in response to receiving the left hip joint position confirmed message, it is determined that the left hip joint component 33L is correctly installed on the corresponding left hip joint position, and the left stepper motor 310L is controlled to stop changing the length of the left leg component 32L.

On the other hand, in response to not receiving the right hip joint position confirmed message from the right hip joint image scanning device 231R among the plurality of image scanning devices in the plurality of second messages, the processor 120 is further configured to determine that the right hip joint component 33R is not correctly installed on the corresponding right hip joint position (step S514→step S515). In step S515, the processor 120 is further configured to instruct the output device 130 to prompt the adjusting right hip joint component message. Further, in an embodiment, the processor 120 can also control the right stepper motor 310R to change the length of the right leg component 32R. During a period in which the length of the right leg component 32R is changed, in response to receiving the right hip joint position confirmed message, it is determined that the right hip joint component 33R is correctly installed on the corresponding right hip joint position, and the right stepper motor 310R is controlled to stop changing the length of the right leg component 32R.

In other words, when the corresponding left/right hip joint position confirmed messages are received by the processor 120, the processor 120 identifies that the left/right hip joint components are correctly installed (worn) on the predetermined left/right hip joint positions, and controls the left/right stepper motors to stop changing the lengths of the left/right leg components.

In response to receiving the left hip joint position confirmed message and the right hip joint position confirmed message, the processor 120 is further configured to determine that the left hip joint component 33L and the right hip joint component 33R are correctly installed on the corresponding left hip joint position and the corresponding right hip joint position respectively (step S514→Yes). Next, in step S517, the processor 120 instructs the output device 130 to prompt a wearing-completed message.

In this embodiment, in response to determining that the left hip joint component 33L and the right hip joint component 33R are correctly installed on the corresponding left hip joint position and the corresponding right hip joint position respectively, the processor 120 can further perform the exoskeleton output correction operation. Details regarding the exoskeleton output correction operation have been described in the first embodiment, which is not repeated hereinafter.

In summary, according to whether a plurality of components of the exoskeleton device are correctly installed on a plurality of corresponding predetermined positions, the exoskeleton wear management system and the exoskeleton wear management method provided by one embodiment of the invention can prompt the user of one or more components among the plurality of components that need to be adjusted. In addition, the exoskeleton wear management system and the exoskeleton wear management method provided by another embodiment of the invention can directly and automatically adjust the position(s) of the one or more components that need to be adjusted and correct the output of the exoskeleton. As a result, the user can correctly wear the exoskeleton device so that applicability, use efficiency and work efficiency of the exoskeleton device are increased and risk of using the exoskeleton device is reduced.

Although the present disclosure has been described with reference to the above embodiments, it will be apparent to one of ordinary skill in the art that modifications to the described embodiments may be made without departing from the spirit of the disclosure. Accordingly, the scope of the disclosure will be defined by the attached claims and not by the above detailed descriptions.

The invention claimed is:

1. An exoskeleton wear management system, adapted to an exoskeleton device worn on a user, the exoskeleton wear management system comprising:
an exoskeleton wear management device, coupled to the exoskeleton device; and
a sensing system, installed on the exoskeleton device and coupled to the exoskeleton wear management device, and configured to continuously sense a current posture of the exoskeleton device to output inertial data corresponding to the current posture to the exoskeleton wear management device,
wherein the exoskeleton wear management device comprises:
an output device;
a storage device, storing an exoskeleton wear management code module; and
a processor, configured to access and execute the exoskeleton wear management code module to realize an exoskeleton wear management method,
wherein the processor is configured to receive first inertial data from the sensing system and determine whether the user is in a sitting posture according to the first inertial data,
wherein in response to determining that the user is in the sitting posture, the processor is further configured to receive second inertial data, wherein the processor is further configured to determine whether each of a plurality of leg components of the exoskeleton device is parallel to a corresponding leg of the user according to the second inertial data,
wherein in response to determining that one of the plurality of leg components of the exoskeleton device in not parallel to the corresponding leg of the user, the processor is further configured to instruct the output device to prompt a message of adjusting the leg component,
wherein an angle sensor array of the sensing system is configured to continuously sense the current posture of the exoskeleton device and output a plurality of angle data corresponding to the current posture to the exoskeleton wear management device,
wherein in response to determining that each of the plurality of leg components of the exoskeleton device is parallel to the corresponding leg of the user, the processor is further configured to instruct the output device to prompt a leg component correctly-worn message.

2. The exoskeleton wear management system according to claim 1,
wherein the processor is further configured to perform a hip joint position management operation,
wherein in the hip joint position management operation, the processor receives a plurality of first angle data form the sensing system, wherein the plurality of first angle data comprise a first left hip joint angle value and a first right hip joint angle value,
wherein the processor determines whether each of a plurality of hip joint components of the exoskeleton device is correctly installed on a corresponding hip joint position according to the plurality of first angle data,
wherein in response to determining that one of the plurality of hip joint components is not correctly installed on the corresponding hip joint position, the processor instructs the output device to prompt a message of adjusting the hip joint component.

3. The exoskeleton wear management system according to claim 2, wherein
in response to determining that each of the plurality of hip joint components is correctly installed on the corresponding hip joint position, the processor instructs the output device to prompt a wearing-completed message, and performs an exoskeleton output correction operation, wherein in the exoskeleton output correction operation,
the processor instructs the output device to prompt a stand-up request message,
wherein the processor receives third angle data form the sensing system,
wherein the processor determines whether the user is in a standing posture according to the third inertial data,
wherein in response to determining that the user is in the standing posture, the processor receives a plurality of second angle data from the sensing system, wherein the plurality of second angle data comprise a second left hip joint angle value, a second right hip joint angle value, a left knee joint angle value and a right knee joint angle value,
wherein the processor calculates a plurality of angle difference data according to the plurality of second angle data and a plurality of historical angle data in a historical database in the storage device, wherein the plurality of historical angle data comprise a historical left hip joint angle value, a historical right hip joint angle value, a historical left knee joint angle value and a historical right knee joint angle value, and the plurality of angle difference data comprise a left hip joint angle difference, a right hip joint angle difference, a left knee joint angle difference and a right knee joint angle difference,
wherein in response to one of the plurality of angle difference data greater than a corresponding allowable threshold, the processor instructs the output device to prompt a standing posture abnormal message,
wherein in response to all of the plurality of angle difference data not greater than the corresponding allowable threshold, the processor adjusts a plurality of output forces of the exoskeleton device corresponding to the plurality of angle difference data according to the plurality of angle difference data, and updates the plurality of historical angle data according to the plurality of second angle data.

4. The exoskeleton wear management system according to claim 3, wherein the sensing system comprises an inertial sensor array, and the inertial sensor array comprises a left inertial sensor installed on a left leg component and a right inertial sensor array installed on a right leg component, wherein the first inertial data comprises first left inertial data from the left inertial sensor and first right inertial data from the right inertial sensor, wherein in the operation of receiving the first inertial data from the sensing system and determining whether the user is in the sitting posture according to the first inertial data, in response to identifying that an X-axis gravitational acceleration absolute value in the first left inertial data is within a predetermined gravitational acceleration range and an X-axis gravitational acceleration absolute value in the first right inertial data is within the predetermined gravitational acceleration range, the processor determines that the user in the sitting posture, wherein the second inertial data comprises N second left inertial data form the left inertial sensor and N second right inertial data from the right inertial sensor, and N is a predetermined positive integer, wherein in the operation of determining whether each of the plurality of leg components of the exoskeleton device is parallel to the corresponding leg of the user according to the second inertial data, the processor calculates a Y-axis acceleration absolute average value and a Z-axis acceleration absolute average value corresponding to the N second left inertial data according to the N second left inertial data, and calculates a Y-axis acceleration absolute average value and a Z-axis acceleration absolute average value corresponding to the N second right inertial data according to the N second right inertial data, wherein in response to identifying that the Y-axis acceleration absolute average value corresponding to the second left inertial data is greater than a Y-axis error threshold or the Z-axis acceleration absolute average value corresponding to the second left inertial data is greater than a Z-axis error threshold, the processor determines that the left leg component of the exoskeleton device is not parallel to a left leg of the user, and in response to identifying that the Y-axis acceleration absolute average value corresponding to the second right inertial data is greater than the Y-axis error threshold or the Z-axis acceleration absolute average value corresponding to the second right inertial data is greater than the Z-axis error threshold, the processor determines that the right leg component of the exoskeleton device is not parallel to a right leg of the user, wherein the third inertial data comprises third left inertial data from the left inertial sensor and third right inertial data from the right inertial sensor, wherein in the operation of determining whether the user is in the standing posture according to the third inertial data, in response to identifying that a Y-axis gravitational acceleration absolute value in the third left inertial data is within a predetermined gravitational acceleration range and a Y-axis gravitational acceleration absolute value in the third right inertial data is within the predetermined gravitational acceleration range, the processor determines that the user is in the standing posture.

5. The exoskeleton wear management system according to claim 2, wherein in the operation of determining whether each of the plurality of hip joint components of the exoskeleton device is correctly installed on the corresponding hip joint position according to the plurality of first angle data, in response to determining that the left hip joint angle value is within a predetermined angle range, the processor determines that a left hip joint component is correctly installed on a left hip joint position; and wherein in response to determining that the right hip joint angle value is within the predetermined angle range, the processor determines that a right hip joint component is correctly installed on a right hip joint position.

6. The exoskeleton wear management system according to claim 2, wherein the exoskeleton wear device further comprises an exoskeleton adjusting system, wherein the exoskeleton adjusting system further comprises a plurality of stepper motors, wherein in response to determining that one of the plurality of hip joint components is not correctly installed on the corresponding hip joint position, the processor controls a stepper motor corresponding to the hip joint component among the plurality of stepper motors to change a length of the leg component corresponding to the hip joint component.

7. The exoskeleton wear management system according to claim 6, wherein the sensing system further comprises an image scanning array, wherein the image scanning array comprises a left knee joint image scanning device and a right knee joint image scanning device, wherein when a first encoded image corresponding to the left knee joint image scanning device is scanned by the left knee joint image scanning device, the left knee joint image scanning device decodes the first encoded image to send a left knee joint position confirmed message to the processor, wherein the left knee joint position confirmed message is configured to indicate that the left knee joint component is correctly installed on a left knee joint position, wherein when a second encoded image corresponding to the right knee joint image scanning device is scanned by the right knee joint image scanning device, the right knee joint image scanning device decodes the second encoded image to send a right knee joint position confirmed message to the processor, wherein the right knee joint position confirmed message is configured to indicate that the right knee joint component is correctly installed on a right knee joint position, wherein in response to receiving the left knee joint position confirmed message and the right knee joint position confit ted message, the processor performs the operation of determining whether the user is in the sitting posture according to the first inertial data, wherein in response to not receiving the left knee joint position confirmed message, the processor instructs the output device to prompt an adjusting left knee joint component message, wherein in response to not receiving the right knee joint position confirmed message, the processor instructs the output device to prompt an adjusting right knee joint component message.

8. The exoskeleton wear management system according to claim 7, wherein the image scanning array further comprises a left hip joint image scanning device and a right hip joint image scanning device, wherein when a third encoded image corresponding to the left hip joint image scanning device is scanned by the left hip joint image scanning device, the left hip joint image scanning device decodes the third encoded image to send a left hip joint position confirmed message to the processor, wherein the left hip joint position confirmed message is configured to indicate that a left hip joint component is correctly installed on a left hip joint position, wherein when a fourth encoded image corresponding to the right hip joint image scanning device is scanned by the right hip joint image scanning device, the right hip joint image scanning device decodes the fourth encoded image to send a right hip joint position confirmed message to the processor, wherein the right hip joint position confirmed message is configured to indicate that a right hip joint component is correctly installed on a right hip joint position, wherein during a period in which a length of a left leg component is changed, in response to receiving the left hip joint position confirmed message, the processor determines that the left hip joint component is correctly installed on the corresponding left hip joint position, and controls a left stepper motor to stop changing the length of the left leg component, wherein during a period in which a length of a right leg component is changed, in response to receiving the right hip joint position confirmed message, the processor determines that the right hip joint component is correctly installed on the corresponding right hip joint position, and controls a right stepper motor to stop changing the length of the right leg component.

9. An exoskeleton wear management method adapted to an exoskeleton wear management system, the exoskeleton wear management system being configured to manage an exoskeleton device worn on a user, wherein the exoskeleton wear management system comprises an exoskeleton wear management device and a sensing system, and the method comprises:

receiving first inertial data from the sensing system and determining whether the user is in a sitting posture according to the first inertial data;

in response to determining that the user is in the sitting posture, receiving second inertial data, and determining whether each of a plurality of leg components of the exoskeleton device is parallel to a corresponding leg of the user according to the second inertial data; and in response to determining that one of the plurality of leg components of the exoskeleton device in not parallel to the corresponding leg of the user, prompting an adjusting leg component message, wherein an angle sensor array of the sensing system is configured to continuously sense a current posture of the exoskeleton device and output a plurality of angle data corresponding to the current posture, wherein in response to determining that each of the plurality of leg components of the exoskeleton device is parallel to the corresponding leg of the user, the method further comprises prompting a correctly-worn message.

10. The exoskeleton wear management method according to claim 9, wherein the method further comprises performing a hip joint position management operation, wherein the hip joint position management operation comprises:

receiving a plurality of first angle data form the sensing system, wherein the plurality of first angle data comprise a first left hip joint angle value and a first right hip joint angle value;

determining whether each of a plurality of hip joint components of the exoskeleton device is correctly installed on a corresponding hip joint position according to the plurality of first angle data;

in response to determining that one of the plurality of hip joint components is not correctly installed on the corresponding hip joint position, prompting an adjusting hip joint component message.

11. The exoskeleton wear management method according to claim 10, further comprising:

in response to determining that each of the plurality of hip joint components is correctly installed on the corresponding hip joint position, prompting a wearing-completed message, and performing an exoskeleton output correction operation, wherein the exoskeleton output correction operation comprises:

prompting a stand-up request message;

receiving third inertial data from the sensing system;

determining whether the user is in a standing posture according to the third inertial data;

in response to determining that the user is in the standing posture, receiving a plurality of second angle data from the sensing system; wherein the plurality of second angle data comprise a second left hip joint angle value, a second right hip joint angle value, a left knee joint angle value and a right knee joint angle value;

calculating a plurality of angle difference data according to the plurality of second angle data and a plurality of historical angle data in a historical database in a storage device, wherein the plurality of historical angle data comprise a historical left hip joint angle value, a historical right hip joint angle value, a historical left knee joint angle value and a historical right knee joint angle value, and the plurality of angle difference data comprise a left hip joint angle difference, a right hip joint angle difference, a left knee joint angle difference and a right knee joint angle difference;

in response to one of the plurality of angle difference data greater than a corresponding allowable threshold, prompting a standing posture abnormal message; and in response to all of the plurality of angle difference data not greater than the corresponding allowable threshold, adjusting a plurality of output forces of the exoskeleton device corresponding to the plurality of angle difference data according to the plurality of angle difference data, and updating the plurality of historical angle data according to the plurality of second angle data.

12. The exoskeleton wear management method according to claim 11, wherein the sensing system comprises an inertial sensor array, and the inertial sensor array comprises a left inertial sensor installed on a left leg component and a right inertial sensor array installed on a right leg component, wherein the first inertial data comprises first left inertial data from the left inertial sensor and first right inertial data from the right inertial sensor, wherein the second inertial data comprises N second left inertial data form the left inertial sensor and N second right inertial data from the right inertial sensor, and N is a predetermined positive integer, wherein the third inertial data comprises third left inertial data from the left inertial sensor and third right inertial data from the right inertial sensor, wherein the step of receiving the first inertial data from the sensing system and determining whether the user is in the sitting posture according to the first inertial data comprises:

in response to identifying that an X-axis gravitational acceleration absolute value in the first left inertial data is within a predetermined gravitational acceleration range and an X-axis gravitational acceleration absolute value in the first right inertial data is within the predetermined gravitational acceleration range, determining that the user in the sitting posture, wherein the step of determining whether each of the plurality of leg components of the exoskeleton device is parallel to the corresponding leg of the user according to the second inertial data comprises:
calculating a Y-axis acceleration absolute average value and a Z-axis acceleration absolute average value corresponding to the N second left inertial data according to the N second left inertial data, and calculating a Y-axis acceleration absolute average value and a Z-axis acceleration absolute average value corresponding to the N second right inertial data according to the N second right inertial data;
in response to identifying that the Y-axis acceleration absolute average value corresponding to the N second left inertial data is greater than a Y-axis error threshold or the Z-axis acceleration absolute average value corresponding to the N second left inertial data is greater than a Z-axis error threshold, determining that the left leg component of the exoskeleton device is not parallel to a left leg of the user; and
in response to identifying that the Y-axis acceleration absolute average value corresponding to the N second right inertial data is greater than the Y-axis error threshold or the Z-axis acceleration absolute average value corresponding to the N second right inertial data is greater than the Z-axis error threshold, determining that the right leg component of the exoskeleton device is not parallel to a right leg of the user,
wherein the step of determining whether the user is in the standing posture according to the third inertial data comprises:
in response to identifying that a Y-axis gravitational acceleration absolute value in the third left inertial data is within the predetermined gravitational acceleration range and a Y-axis gravitational acceleration absolute value in the third right inertial data is within the predetermined gravitational acceleration range, determining that the user is in the standing posture.

13. The exoskeleton wear management method according to claim 10, wherein the step of determining whether each of the plurality of hip joint components of the exoskeleton device is correctly installed on the corresponding hip joint position according to the plurality of first angle data comprises:
in response to determining that the left hip joint angle value is within a predetermined angle range, determining that a left hip joint component is correctly installed on a left hip joint position; and
in response to determining that the right hip joint angle value is within the predetermined angle range, determining that a right hip joint component is correctly installed on a right hip joint position.

14. The exoskeleton wear management method according to claim 10, wherein the exoskeleton wear device further comprises an exoskeleton adjusting system, wherein the exoskeleton adjusting system further comprises a plurality of stepper motors, and the method further comprises:
in response to determining that one of the plurality of hip joint components is not correctly installed on the corresponding hip joint position, controlling a stepper motor corresponding to the hip joint component among the plurality of stepper motors to change a length of the leg component corresponding to the hip joint component.

15. The exoskeleton wear management method according to claim 14, wherein the sensing system further comprises an image scanning array, wherein the image scanning array comprises a left knee joint image scanning device and a right knee joint image scanning device, and the method further comprises:
when a first encoded image corresponding to the left knee joint image scanning device is scanned by the left knee joint image scanning device, decoding the first encoded image by the left knee joint image scanning device to send a left knee joint position confirmed message, wherein the left knee joint position confirmed message is configured to indicate that a left knee joint component is correctly installed on a left knee joint position;
when a second encoded image corresponding to the right knee joint image scanning device is scanned by the right knee joint image scanning device, decoding the second encoded image by the right knee joint image scanning device to send a right knee joint position confirmed message, wherein the right knee joint position confirmed message is configured to indicate that a right knee joint component is correctly installed on a right knee joint position;
in response to receiving the left knee joint position confirmed message and the right knee joint position confirmed message, performing the step of determining whether the user is in the sitting posture according to the first inertial data;
in response to not receiving the left knee joint position confirmed message, prompting an adjusting left knee joint component message; and
in response to not receiving the right knee joint position confirmed message, prompting an adjusting right knee joint component message.

16. The exoskeleton wear management method according to claim 15, wherein the image scanning array further comprises a left hip joint image scanning device and a right hip joint image scanning device, and the method further comprises:
when a third encoded image corresponding to the left hip joint image scanning device is scanned by the left hip joint image scanning device, decoding the third encoded image by the left hip joint image scanning device to send a left hip joint position confirmed message, wherein the left hip joint position confirmed message is configured to indicate that a left hip joint component is correctly installed on a left hip joint position;
when a fourth encoded image corresponding to the right hip joint image scanning device is scanned by the right hip joint image scanning device, decoding the fourth encoded image by the right hip joint image scanning device to send a right hip joint position confirmed message, wherein the right hip joint position confirmed message is configured to indicate that a right hip joint component is correctly installed on a right hip joint position;
during a period in which the length of a left leg component is changed, in response to receiving the left hip joint position confirmed message, determining that the left hip joint component is correctly installed on the corresponding left hip joint position, and controlling a left stepper motor to stop changing the length of the left leg component; and
during a period in which the length of a right leg component is changed, in response to receiving the right hip joint position confirmed message, determining that the right hip joint component is correctly installed on the corresponding right hip joint position, and controlling a right stepper motor to stop changing the length of the right leg component.

\* \* \* \* \*